US012279776B2

(12) United States Patent
O'Halloran et al.

(10) Patent No.: US 12,279,776 B2
(45) Date of Patent: *Apr. 22, 2025

(54) IMPLANTABLE MEDICAL DEVICE

(71) Applicant: University of Galway, Galway (IE)

(72) Inventors: Tony O'Halloran, County Galway (IE); John Thompson, Dublin (IE); Martin O'Halloran, County Galway (IE); Faisal Sharif, Galway (IE)

(73) Assignee: UNIVERSITY OF GALWAY, Galway (IE)

( * ) Notice: Subject to any disclaimer, the term of this patent is extended or adjusted under 35 U.S.C. 154(b) by 38 days.

This patent is subject to a terminal disclaimer.

(21) Appl. No.: 18/333,864

(22) Filed: Jun. 13, 2023

(65) Prior Publication Data

US 2023/0320734 A1 Oct. 12, 2023

Related U.S. Application Data

(63) Continuation of application No. 16/500,863, filed as application No. PCT/EP2018/058799 on Apr. 5, 2018, now Pat. No. 11,712,247.

(30) Foreign Application Priority Data

Apr. 5, 2017 (EP) ..................................... 17165091

(51) Int. Cl.
*A61B 17/12* (2006.01)
*A61B 18/14* (2006.01)
(Continued)

(52) U.S. Cl.
CPC .. *A61B 17/12122* (2013.01); *A61B 17/12031* (2013.01); *A61B 17/12136* (2013.01);
(Continued)

(58) Field of Classification Search
CPC .............. A61B 17/12; A61B 17/12122; A61B 17/12031; A61B 17/12136; A61B 17/0057; A61B 18/14
See application file for complete search history.

(56) References Cited

U.S. PATENT DOCUMENTS 4,909,789 A   3/1990  Taguchi et al.
5,573,530 A   11/1996 Fleury et al.
(Continued)

FOREIGN PATENT DOCUMENTS

WO   2001087168 A1   11/2001
WO   2002069783 A2    9/2002
(Continued)

OTHER PUBLICATIONS

International Search Report for corresponding Application No. PCT/EP2018/058799, dated Oct. 11, 2018 (4 pages).

*Primary Examiner* — Vi X Nguyen
(74) *Attorney, Agent, or Firm* — Bookoff McAndrews, PLLC

(57) ABSTRACT

A device for occlusion of a body lumen comprises an implantable occlusion apparatus (3) operably attached to an elongated catheter member (4) configured for transluminal delivery and deployment of the occlusion apparatus in the body lumen. The occlusion apparatus comprises a radially expansible element (5) detachably attached to the elongated catheter member, and adjustable between a contracted orientation suitable for 10 transluminal delivery and a deployed orientation configured to occlude the body lumen, an energy delivery element (6, 14, 21) configured to deliver energy to surrounding tissue to heat the tissue, and a sensor (7) configured to detect a parameter of the wall of the body lumen. The energy delivery element (6, 14, 21) and sensor (7) are axially movable independently of the radially expansible element whereby, in use, the energy delivery 15
(Continued)

element and sensor can be transluminally retracted leaving the radially expansible element in-situ occluding the body lumen.

9 Claims, 17 Drawing Sheets

(51) Int. Cl.
    *A61B 17/00*     (2006.01)
    *A61B 18/00*     (2006.01)

(52) U.S. Cl.
    CPC .... *A61B 17/12172* (2013.01); *A61B 18/1492* (2013.01); *A61B 2017/00026* (2013.01); *A61B 2017/00057* (2013.01); *A61B 2017/00084* (2013.01); *A61B 2017/00243* (2013.01); *A61B 2017/00632* (2013.01); *A61B 2017/12054* (2013.01); *A61B 2018/00023* (2013.01); *A61B 2018/00267* (2013.01); *A61B 2018/1475* (2013.01)

(56) References Cited

U.S. PATENT DOCUMENTS

| | | | |
|---|---|---|---|
| 5,928,260 A * | 7/1999 | Chin | A61B 17/12113 604/107 |
| 6,454,775 B1 | 9/2002 | Demarais et al. | |
| 6,652,548 B2 | 11/2003 | Evans et al. | |
| 2002/0169473 A1 | 3/2002 | Sepetka | |
| 2004/0219028 A1 | 11/2004 | Demarais et al. | |
| 2010/0076416 A1 | 3/2010 | Hoey | |
| 2013/0197555 A1 | 8/2013 | Schaer | |
| 2018/0161039 A1 * | 6/2018 | Harks | A61B 17/12122 |
| 2019/0350567 A1 * | 11/2019 | Cummins | A61B 17/00008 |

FOREIGN PATENT DOCUMENTS

| | | |
|---|---|---|
| WO | 2003041602 A2 | 5/2003 |
| WO | 2005122939 A1 | 12/2005 |
| WO | 2007001981 A2 | 1/2007 |
| WO | 2012109297 A2 | 8/2012 |
| WO | 2013009872 A1 | 1/2013 |
| WO | 2013109756 A2 | 7/2013 |
| WO | 2014141226 A1 | 9/2014 |
| WO | 2016202708 A1 | 12/2016 |

* cited by examiner

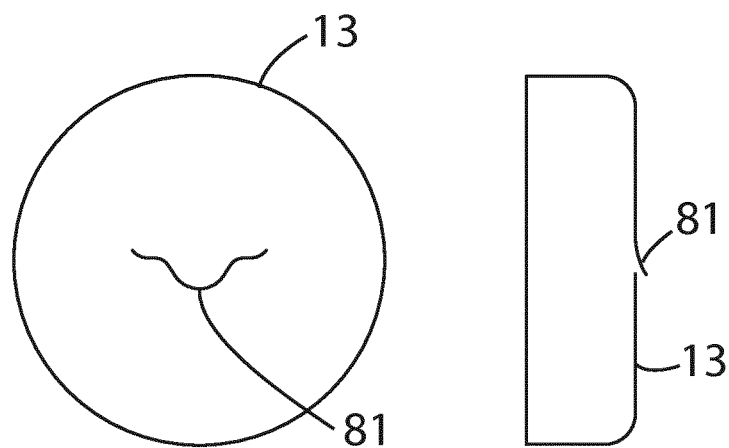
Figure 14A
Figure 14B
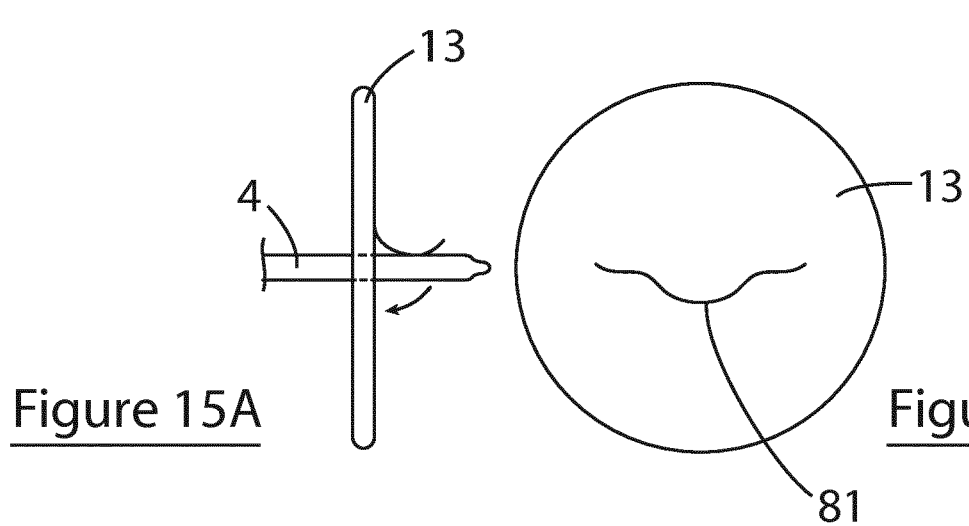
Figure 15A
Figure 15B
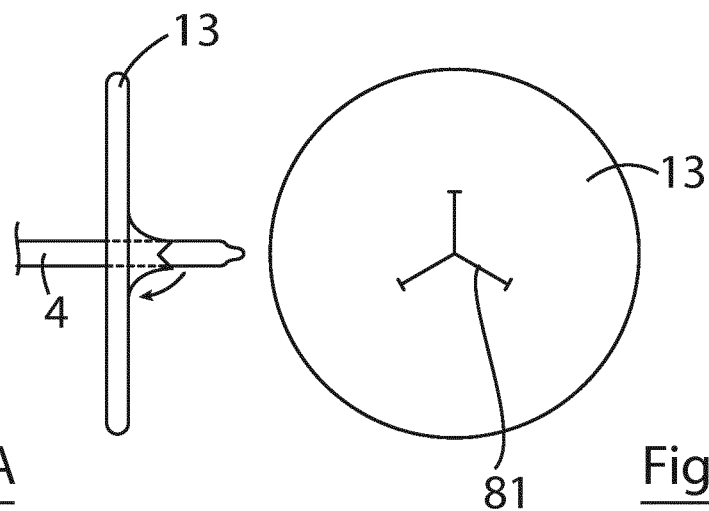
Figure 16A
Figure 16B

IMPLANTABLE MEDICAL DEVICE

CROSS-REFERENCE TO RELATED APPLICATION(S)

This patent application is a continuation of and claims the benefit of priority to U.S. application Ser. No. 16/500,863, filed on Oct. 4, 2019, which is a National Stage Application under 35 U.S.C. § 371 of International Application No. PCT/EP2018/058799, filed Apr. 5, 2018, which claims priority to EP patent application Ser. No. 17/165,091.4, filed on Apr. 5, 2017, the entireties of all of which are incorporated herein by reference.

FIELD OF THE INVENTION

The present invention relates to an implantable medical device to heat tissue. In particular, the invention relates to an implantable medical device for implantation in a body lumen and occlusion and optionally devascularisation of the body lumen. In another aspect, the invention relates to a method of occlusion of a body lumen. In another aspect, the invention relates to a method of prevention of atrial fibrillation and/or thrombotic events.

BACKGROUND TO THE INVENTION

Atrial fibrillation (AF) is a common cardiac rhythm disorder affecting an estimated 6 million patients in the United States alone. AF is the second leading cause of stroke in the United States and may account for nearly one-third of strokes in the elderly. As our population continues to age, this problem may become even more prevalent. In greater than 90% of cases where a blood clot (thrombus) is found in the AF patient, the clot develops in the left atrial appendage (LAA) of the heart. The irregular heart beat in AF causes blood to pool in the left atrial appendage, because clotting occurs when blood is stagnant, clots or thrombi may form in the LAA. These blood clots may dislodge from the left atrial appendage and may enter the cranial circulation causing a stroke, the coronary circulation causing a myocardial infarction, the peripheral circulation causing limb ischemia, as well as other vascular beds. The LAA is a muscular pouch of heart attached to the left atrium. Mechanical occlusion of the LAA may result in a reduction of the incidence of stroke in AF patients, and there is growing interest in both surgical and endovascular methods to remove isolate the LAA.

Anti-clotting drugs may be used to prevent strokes in patients diagnosed with AF. However, many people cannot take such drugs because of potential side effects. Drug therapy may also cause bleeding and may be difficult to control because determining dosage is challenging. Recent studies indicate that elimination of the LAA, through occlusion or closure, may prevent thrombi from forming in the LAA and thus may reduce the incidence of stroke in patients diagnosed with AF. As such, occlusion or closure of the LAA may significantly reduce the incidence of stroke in patients with atrial fibrillation and without the complications of drug therapy.

Historically, LAA's have sometimes been modified surgically, via suturing, clipping or excision to reduce the risk imposed by atrial fibrillation. In recent years, devices which may be delivered percutaneously into the left atrial appendage have been introduced. The basic function of these devices is to exclude the volume within the appendage with an implant which then allows blood within the appendage to safely thrombose and then to be gradually incorporated into cardiac tissue. This can leave a smooth, endothelialized surface where the appendage used to be.

New devices to percutaneously occlude the LAA have been developed for stroke prophylaxis and seem promising. These new devices include the use of a clip to clamp the LAA shut, the use of a snare to wall off the LAA, the use of an umbrella device to expand the LAA, the use of a device which may close the LAA but not obliterate it, and the use of a device which may fill the LAA without closing it. Data on the safety and efficacy of these devices must be considered over time. These new devices are early in clinical trials for human application and have several limitations. For instance, use of the clip to clamp the LAA shut may not get down to the base of the LAA, may leave a residual stump or leak, may result in a clot forming, and may require open surgery. Use of the snare may leave a residual stump or leak, may be less controlled, and may not be possible if adhesions are located around the heart. Use of the umbrella device may require the patient to be on blood thinners since it is made out of a foreign material and does not occlude and obliterate the LAA simultaneously. Use of a device which may close the LAA without obliterating it, and use of a device which may obliterate the LAA without closing it are both incomplete solutions which may experience leakage, which may require blood thinners due to the use of synthetic materials, or which may experience other types of issues.

More recent devices proposed for occlusion of the LAA and prevention/treatment of atrial fibrillation and LAA-associated thrombotic events are described. WO2012/109297 describes an implantable device having an expandable LAA-occluding barrier and anchor configured for engagement of the ostium of the LAA, a pacing module for treatment of atrial fibrillation, and a sensor for detecting the electrical activity of the heart indicative of arrhythmia. WO2013/009872 describes a LAA-occluding device configured to inject a filler material into the LAA, and including a transponder unit configured to detect and relay to an external base station data electrical parameters of the LAA tissue. WO2016/202708 describes an implantable device having a LAA occluding body, electrodes configured to heat LAA tissue with a view to electrical isolation of the LAA, and sensors configured to determine heat or electrical activity of the LAA, which signals are used as feedback to control the heating of the tissue. While these devices are capable of occluding LAA's having regular openings, they are not suitable for use with LAA's having irregular shaped openings. In addition, while the devices may be operable to monitor and achieve electrical isolation of the LAA, in many cases they will not prevent subsequent atrial fibrillation events as electrical isolation achieved with the devices is reversible. A further problem with these devices is that the connector between the delivery catheter and the expandable barrier is disposed on the left atrial side of the barrier, and exposed to circulating blood, which can cause DRT (device-related thrombus) formation.

It is an object of the invention to overcome at least one of the above-referenced problems.

SUMMARY OF THE INVENTION

These objects are met by the provision of a device for occlusion of a body lumen (for example the LAA) comprising an implantable occlusion apparatus operably and detachably attached to an elongated catheter member configured for transluminal delivery and deployment of the occlusion apparatus in the body lumen. The occlusion apparatus typically comprises a radially expansible element that is adjustable between a contracted orientation suitable for transluminal delivery and a deployed orientation configured to occlude the body lumen. The occlusion apparatus is typically configured to deliver energy to surrounding tissue, for example to heat the tissue. The occlusion apparatus typically comprises a sensor to detect a parameter of the wall of the body lumen, for example detect blood flow in the wall of the body lumen. In a preferable embodiment, the energy delivery element and sensor are separate from the radially expansible element, and can be moved axially independently of the radially expansible body. This allows the energy delivery element and sensor to be retracted after use, leaving the radially expansible element in-situ in the body lumen occluding the body lumen. Thus, the device can be transluminal delivered to a body lumen such as the LAA, deployed in-situ in the LAA where the radially expansible element is expanded to engage the surrounding wall of the LAA, the tissue treated to electrically isolate and devascularize the LAA by means of the energy delivery element, and the treatment monitored using the sensor, and when the treatment is complete the energy delivery element and sensor can be retracted through the catheter member leaving the radially expansible element in-situ in the LAA, to prevent any further blood flow into the now devascularized LAA.

In another embodiment, the energy delivery element and/or sensor is integrated into the radially expansible element. In this embodiment, the catheter member is configured for releasable attachment to the occlusion apparatus, whereby upon release of the catheter member from the occlusion apparatus the catheter member may be retracted leaving the occlusion body in-situ. In one embodiment, a proximal side of the radially expansible member comprises a cover, generally a fluid-tight cover, and the connecting hub between the elongated catheter member and the radially expansible element is recessed distally of the cover. The serves to separate the connecting hub (which is prone to be a cause of DRT—device related thrombus formation) from circulating blood flow on the proximal side of the radially expansible member. The cover typically comprises a self-closing aperture configured to receive the elongated catheter member and close on detachment and retraction of the elongated catheter member.

In a further aspect, the invention provides a device for occlusion of a body lumen comprising an implantable occlusion apparatus operably and detachably attached to an elongated catheter member configured for transluminal delivery and deployment of the occlusion apparatus in the body lumen, the occlusion apparatus comprising:
- a radially expansible element that is adjustable between a contracted orientation suitable for transluminal delivery and a deployed orientation configured to occlude the body lumen;
- an energy delivery element configured to deliver energy to surrounding tissue to heat the tissue; and
- optionally, a sensor configured to detect a parameter of the wall of the body lumen, In one embodiment, the device comprises a sensor configured to detect a parameter of the wall of the body lumen.

In one embodiment, the energy delivery element and/or sensor are generally axially movable independently of the radially expansible element whereby, in use, the energy delivery element and/or sensor can be transluminally retracted leaving the radially expansible element in-situ occluding the body lumen. In this embodiment, the catheter member is detachably attached to the radially expansible element of the occlusion apparatus. The radially expansible element comprises an aperture, typically an axial aperture, for receipt of the energy delivery element and/or sensor.

This embodiment of the device of the invention allows a device to be transluminally delivered to a body lumen, for example the Left Atrial Appendage (LAA), where the radially expansible element is deployed to occlude the body lumen, and the energy delivery element is deployed to come into contact with the wall of the body lumen distal to, or surrounding, the radially expansible member. Delivery of energy to the tissue by the energy delivery element causes ablation of the surrounding tissue, which results in devascularisation and electrical isolation of the body lumen. The sensor is generally employed to detect a parameter of the wall of the body lumen that can be correlated with devascularisation and electrical isolation, for example detection of blood flow in the body lumen. The device is configured to deploy the sensor to detect a parameter of the wall of the body lumen adjacent or distal to the radially expansible member. The sensor can detect when blood flow in the body lumen has stopped, and can therefore inform the amount of energy delivered to the tissue by the energy delivery element. The provision of an energy delivery element and/or sensor (preferably both) that is axially movable independent of the radially expansible member allows the retraction of the energy delivery element and/or sensor after the tissue has been treated, leaving the radially expansible element in-situ in the body lumen, occluding the body lumen.

In one embodiment, the energy delivery element and sensor are configured for axial retraction into the catheter member. They may be operably connected together, to allow both to be retracted simultaneously, or they may be separate to allow axial movement of one relative to the other.

In another embodiment, the energy delivery element and sensor are associated with the radially expansible element and configured to be left in-situ in the body lumen when the catheter member is detached from the occlusion body.

In one embodiment, the energy delivery element comprises a radially expansible body configured for adjustment from a contracted configuration suitable for transluminal delivery and retraction, and a deployed configuration suitable for engagement with surrounding tissue of the body lumen.

In one embodiment, the radially expansible body is disposed within the radially expansible element and is configured such that one or more parts of the radially expansible body project through the radially expansible element when in a deployed configuration.

In one embodiment, the radially expansible body is self-expansible and biased to adapt a deployed orientation. In this embodiment, the device typically comprises a sheath configured to restrain the radially expansible body in a contracted orientation, whereby the device is configured for axial movement of the sheath relative to the radially expansible body between a first position in which the sheath covers the radially expansible body and a second position in which the sheath does not cover the radially expansible body. In one preferred embodiment, the sheath is configured for movement relative to the radially expansible body. In one embodiment, the sheath is configured for movement from a first position within or distal to the radially expansible body to a second position proximal of the first position, and ideally a second position proximal to the radially expansible element. Distal withdrawal of the sheath relative to the radially expansible body effects deployment of the energy delivery radially expansible body. In another embodiment, the sheath is configured for movement relative to the radially expansible body.

In another embodiment, the device comprises elongated distal and proximal control arms configured to adjust the radially expansible body between the contracted and deployed configurations. The distal arm is typically operably connected to (or near) a distal end of the radially expansible body and a proximal control arm is operably connected to (or near) a proximal end of the radially expansible body, whereby relative axial movement of the arms causes deployment or contraction of the radially expansible body. The distal and proximal arms are configured to pass through the aperture in the radially expansible element.

In one embodiment, the radially expansible body comprises a plurality of interconnected V-shaped struts arranged radially around a common axis. It will be appreciated that the struts do not need to be v-shaped, but may have another shape suitable for expansion and contraction, such as a W-shape or a U-shape. The V-shaped struts are particularly useful as the inflection point of the apex of the V is small enough to pass through the wall of the surrounding radially expansible element (when the radially expansible body is disposed within the radially expansible element) and come into contact with the surrounding tissue.

In another embodiment, the radially expansible body comprises a plurality of outwardly curved elements. This is similar to a "palm-tree" shape. Generally, the elements are self-expansible into the outwardly curved orientation, and may be formed from a shape-memory material such as NITINOL to facilitate this embodiment. Typically, this embodiment of the device employs a sheath configured to restrain the radially expansible body in a contracted orientation, whereby the device is configured for axial movement of the sheath relative to the radially expansible body between a first position in which the sheath covers the radially expansible body and a second position in which the sheath does not cover the radially expansible body.

In one embodiment, the energy delivery element and sensor are operably connected and configured for co-deployment and co-retraction.

In one embodiment, the sensor forms part of the radially expansible body. Thus, in the V-shaped strut embodiment, one or more of the struts may be energy delivery elements and one or more of the struts may be sensors.

In one embodiment, the energy delivery element and sensor are axially movable independently of each other. This allows movement of the sensor distally of the energy delivery element, which may be preferred is some embodiments where it is advantageous to measure a parameter of the wall of the body lumen distally of where the energy delivery element treats the wall of the body lumen.

In one embodiment, the sensor is configured for axial movement distally of the energy delivery element and retraction proximally of the radially expansible element.

In one embodiment, the sensor extends axially through the centre of the radially expansible element. In one embodiment, the energy delivery element extends axially through the centre of the radially expansible element.

In one embodiment, the radially expansible element comprises a wire mesh. In one embodiment, the wire mesh is configured to allow the parts of the energy delivery element come into contact with surrounding tissue through the wire mesh.

In one embodiment, the radially expansible element is self-expansible and biased to adapt a deployed orientation.

In one embodiment, the radially expansible element comprises proximal part having a substantially toroidal shape and the distal part is substantially cylindrical.

In one embodiment, the device is configured for adjustment from a first configuration in which the radially expansible element, sensor and energy delivery element are disposed within a distal end of the catheter member, a second configuration in which the radially expansible element, sensor and energy delivery element are exposed distally of a distal end of the catheter member and in which the radially expansible element is in a deployed configuration and the energy delivery element is in contact with the surrounding tissue, and a third configuration in which the energy delivery element and sensor are retracted proximally of the radially expansible element and the catheter member is detached from the radially expansible element.

In one embodiment, the energy delivery element comprises a radially expansible body configured for adjustment from a contracted configuration suitable for transluminal delivery and retraction, and a deployed configuration suitable for engagement with surrounding tissue of the body lumen, wherein in the second configuration the radially expansible body is deployed within the radially expansible element.

In one embodiment, the third configuration includes an initial configuration in which the radially expansible body is in a contracted configuration within the radially expansible element, and a subsequent configuration in which the radially expansible body is retracted proximally of the radially expansible element.

In one embodiment, the device comprises an expandable balloon configured for deployment within or distal to the radially expansible element. The balloon may be deployed to seal the body lumen. In this embodiment, the sensor (or at least one of the sensors) is disposed distally of the expandable balloon.

In one embodiment, the energy delivery element is disposed within the expandable balloon and is preferably configured for deployment with the balloon. For example, the energy delivery element could be attached to a wall of the balloon such that when the balloon is inflated and the walls come into contact with the wall of the body lumen, the energy delivery element also comes into contact with the wall via the balloon material. In one embodiment, the balloon is a cryoballoon (i.e. configured to freeze tissue). In one embodiment, the balloon is configured fro delivering RF energy. In one embodiment, the expandable balloon is disposed within the radially expansible element.

In one embodiment, the device comprises a lumen having an opening disposed distally of the radially expansible element, in which the lumen is configured for delivering fluid or substances or withdrawing fluid or matter from the body lumen, for example flushing the body lumen with liquid and/or withdrawing liquid (i.e. blood) or clots from the body lumen or drawing a vacuum in the body lumen. In an embodiment in which the device comprises an inflatable balloon, the balloon is typically disposed on the lumen and the opening of the lumen is typically disposed distally of the inflatable balloon. In this embodiment, the balloon is inflated to seal the body lumen distally of the balloon, and the lumen (or optionally plurality of lumens) are actuated to flush the end of the body lumen with a flushing liquid such as saline. This has been found to improve the accuracy of the sensor, especially when optical sensors are employed.

In another embodiment, the balloon is configured for deployment distally of the radially expansible element. In this embodiment, the device typically comprises a lumen that extends distally of the radially expansible element, and in which the balloon is mounted to the lumen. The sensor may be disposed on or within the lumen.

In one embodiment, the wall of the radially expansible element comprises one or more anchors (i.e. hooks or barbs or the like) configured for engagement with the surrounding tissue. In an embodiment in which the device comprises a balloon configured for inflation within the radially expansible element, the balloon when inflated pushes the anchors into engagement with the tissue.

In one embodiment, the distal end of the radially expansible element comprises one or more sidewall portions that are adjustable from an inwardly depending position to an outwardly depending, wall engaging, position, wherein one or more anchors are disposed on the sidewall portions. In this embodiment, the anchors cannot engage the wall of the body lumen until the balloon is inflated which pushes the sidewall portions radially outwardly and into engagement with the tissue, locking the radially expansible member in-situ in the body lumen. In one embodiment, the energy delivery element includes an electrical circuit which is completed when the sidewall portions are adjusted from the inwardly depending position to the outwardly depending, wall engaging, position.

Thus, in one aspect, the invention provides a device for occlusion of a body lumen comprising an implantable occlusion apparatus operably and detachably attached to an elongated catheter member configured for transluminal delivery and deployment of the occlusion apparatus in the body lumen, the occlusion apparatus comprising:
  a radially expansible element that is adjustable between a contracted orientation suitable for transluminal delivery and a deployed orientation configured to occlude the body lumen;
  a cover disposed on a proximal side of the radially expansible element;
  an energy delivery element configured to deliver energy to surrounding tissue to heat the tissue, and
  optionally, a sensor configured to detect a parameter of the wall of the body lumen,
characterised in that the elongated catheter member is connected to the radially expansible element by a connecting hub, wherein the connecting hub is disposed distally of the cover, and wherein the cover typically comprises a self-closing aperture configured to receive the elongated catheter member and close on detachment and retraction of the elongated catheter member.

In a further aspect, the invention provides a device for occlusion of a body lumen comprising an implantable occlusion apparatus operably and detachably attached to an elongated catheter member configured for transluminal delivery and deployment of the occlusion apparatus in the body lumen, the occlusion apparatus comprising:
  a radially expansible element that is adjustable between a contracted orientation suitable for transluminal delivery and a deployed orientation configured to occlude the body lumen;
  an energy delivery element configured to deliver energy to surrounding tissue to heat the tissue; and
  a sensor configured to detect a parameter of the wall of the body lumen,
characterised in that the sensor is an optical sensor configured to detect changes in blood flow in the wall of the body lumen.

In a further aspect, the invention provides a device for occlusion of a body lumen comprising an implantable occlusion apparatus operably and detachably attached to an elongated catheter member configured for transluminal delivery and deployment of the occlusion apparatus in the body lumen, the occlusion apparatus comprising:
  a radially expansible element that is adjustable between a contracted orientation suitable for transluminal delivery and a deployed orientation configured to occlude the body lumen;
  an energy delivery element configured to deliver energy to surrounding tissue to heat the tissue; and
  optionally, a sensor configured to detect a parameter of the wall of the body lumen,
characterised in that the radially expansible element comprises a body having a distal part and a proximal part, wherein the proximal part has greater radial deformability that the distal part.

In a further aspect, the invention provides a device for occlusion of a body lumen comprising an implantable occlusion apparatus operably and detachably attached to an elongated catheter member configured for transluminal delivery and deployment of the occlusion apparatus in the body lumen, the occlusion apparatus comprising:
  a radially expansible element that is adjustable between a contracted orientation suitable for transluminal delivery and a deployed orientation configured to occlude the body lumen;
  an energy delivery element configured to deliver energy to surrounding tissue to heat the tissue; and
  optionally, a sensor configured to detect a parameter of the wall of the body lumen,
characterised in that the radially expansible element comprises proximal part having a substantially toroidal shape and the distal part is substantially cylindrical.

In a further aspect, the invention provides a device for occlusion of a body lumen comprising an implantable occlusion apparatus operably and detachably attached to an elongated catheter member configured for transluminal delivery and deployment of the occlusion apparatus in the body lumen, the occlusion apparatus comprising:
  a radially expansible element that is adjustable between a contracted orientation suitable for transluminal delivery and a deployed orientation configured to occlude the body lumen;
  an energy delivery element configured to deliver energy to surrounding tissue to heat the tissue; and
  optionally, a sensor configured to detect a parameter of the wall of the body lumen,
characterised in that the radially expansible element comprises a proximal radially expansible body and a distal radially expansible body, wherein the radially expansible bodies are axially adjustable from an axially spaced apart orientation to an axially adjacent, tissue gathering, orientation.

In a further aspect, the invention provides a device for occlusion of a body lumen comprising an implantable occlusion apparatus operably and detachably attached to an elongated catheter member configured for transluminal delivery and deployment of the occlusion apparatus in the body lumen, the occlusion apparatus comprising:
  a radially expansible element that is adjustable between a contracted orientation suitable for transluminal delivery and a deployed orientation configured to occlude the body lumen;
  an energy delivery element configured to deliver energy to surrounding tissue to heat the tissue, and
  a sensor configured to detect a parameter of the wall of the body lumen,
characterised in that the radially expansible element comprises a central axial conduit, and wherein the sensor is configured for movement relative to the radially expansible element through the conduit from a retracted orientation to a deployed orientation in which the sensor is deployed distally of the radially expansible body.

In a further aspect, the invention provides a device for occlusion of a body lumen comprising an implantable occlusion apparatus operably and detachably attached to an elongated catheter member configured for transluminal delivery and deployment of the occlusion apparatus in the body lumen, the occlusion apparatus comprising:

a radially expansible element that is adjustable between a contracted orientation suitable for transluminal delivery and a deployed orientation configured to occlude the body lumen;

an energy delivery element configured to deliver energy to surrounding tissue to heat the tissue, and a sensor configured to detect a parameter of the wall of the body lumen, characterised in that the device comprises an inflatable balloon configured for inflation within or distal to the radially expansible element to preferably seal the body lumen. In one embodiment, the energy delivery element is disposed within the inflatable balloon, and is configured to deploy when the balloon inflates. In one embodiment, the balloon is mounted on an axial lumen having a distal opening disposed distally of the balloon, wherein the lumen is configured for flushing the body lumen distal of the balloon with a flushing fluid, for example a saline solution.

In one embodiment, the body lumen is a left atrial appendage (LAA).

In one embodiment, the sensor is configured to detect changes in blood flow in the wall of the body lumen. In one embodiment, the sensor is an optical sensor.

In one embodiment, the sensor is disposed at or distally of the radially expansible element and configured to detect vascularisation in the wall of the body lumen at or distal of the radially expansible element.

In one embodiment, the sensor measures light reflected by tissue. In another embodiment, the sensor measures light transmitted through tissue. In one embodiment, the sensor is selected from a pulse oximetry sensor or a photoplesmography sensor.

In one embodiment, the sensor comprises a plurality of sensing elements which extend radially outwardly from a central axis of the device.

In one embodiment, the sensor is disposed within the catheter member and configured for axial movement relative to the occlusion apparatus through a central conduit in the occlusion apparatus from a retracted position to an extended position distal of the occlusion apparatus.

In one embodiment, the device comprises a temperature sensor configured to detect the temperature of the surrounding tissue. Generally, the temperature sensor is disposed on or in the region of the radially expansible element.

In one embodiment, the radially expansible element has a central conduit extending axially through the body. In one embodiment, a proximal side of the radially expansible element comprises a self-closing aperture covering an opening of the central conduit. In one embodiment, the central conduit is configured to receive the elongated catheter member, wherein the self-closing aperture is configured to close on detachment and retraction of the elongated catheter member.

In one embodiment, one or more lumens extend through the central conduit. In one embodiment, the or each lumen is movable axially relative to the radially expansible body. In one embodiment, at least one lumen is configured to provide fluid to, or withdraw fluid from, the body lumen distally of the radially expansible element. In one embodiment, at least one lumen contains the sensor. In one embodiment, at least one lumen contains an energy delivery element.

In one embodiment, the elongated catheter member is connected to the radially expansible element by a connecting hub, wherein the connecting hub is disposed distally of the self-closing aperture.

In one embodiment, the radially expansible element is selected from an inflatable balloon and a wireframe structure, for example a braided mesh. In one embodiment, the wireframe structure is formed from a shape memory material, i.e. nitinol. In one embodiment, the wireframe structure has a toroid shape.

In one embodiment, the radially expansible element comprises a cover on its proximal side configured to seal the body lumen. The cover may be integral with the radially expansible element, or may be separate. The cover may be a fine mesh, or a woven material.

In one embodiment, the cover is configured to promote epithelial cell proliferation. In one embodiment, the cover comprises biological material selected from growth factors, cells, tissue, and extracellular matrix. In one embodiment, the cover comprises a biological scaffold, for example a collagen scaffold formed by e.g. lyophilisation.

In one embodiment, the device comprises a retractable delivery sheath adjustable between a delivery configuration in which the sheath covers the radially expansible element and constrains the element in a contracted orientation and a deployed configuration in which the sheath is retracted to expose the radially expansible element.

In one embodiment, the radially expansible element comprises a body having a distal part and a proximal part, wherein the proximal part has greater radial deformability that the distal part.

In one embodiment, the proximal part has a substantially toroidal shape and the distal part is substantially cylindrical.

In one embodiment, the energy delivery element is disposed on the radially expansible element.

In one embodiment, the energy delivery element is configured to delivery energy along the circumference of the radially expansible element. The energy delivery element may be spatially continuous along the circumference of the radially expansible element, or may be spatially intermittent.

In one embodiment, the energy delivery element comprises a plurality of energy delivery elements configured to extend radially distally of the radially expansible element.

In one embodiment, the energy delivery element comprises a central tissue ablation electrode and a plurality of electrodes disposed coaxially about the central electrode and extending radially outwardly.

In one embodiment, the radially expansible element comprises a proximal radially expansible body and a distal radially expansible body, wherein the radially expansible bodies are axially adjustable together and apart. The distal and proximal bodies may be formed from a single wireframe structure or from separate wireframe structures.

In one embodiment, the device comprises a force control mechanism operatively connected to both radially expansible bodies and adapted to provide controlled resistance to the movement of one body relative to the other. In one embodiment, the force control mechanism is torque actuating system, which is configured to limit the contraction of the distal and proximal bodies together by force control.

In one embodiment, the proximal radially expansible body and distal radially expansible body are operably connected by a connector. In one embodiment, the conduit extends through the connector.

In one embodiment, the device comprises a brake mechanism configured to lock the radially expansible bodies in an axially desired position. In one embodiment, the brake mechanism is associated with the connector. In one embodiment, the connector comprises a ratchet connection, a snap-fit connection, a corkscrew connection, an interference fit connection, or a threaded connection.

In one embodiment, the device is configured for adjustment between a delivery configuration in which the distal and proximal bodies are spaced apart and contracted, a first deployment configuration in which the distal body is deployed, a second deployment configuration in which the proximal body is deployed, a third deployment configuration in which the distal and proximal bodies are adjusted to the axially adjacent configuration and the brake mechanism is actuated, and a final deployment configuration is which the elongated catheter body is detached from the occlusion body.

In one embodiment, the retractable delivery sheath is adjustable between at least three positions including the delivery configuration, a partially deployed configuration in which the sheath is retracted to expose the distal body but covers the proximal body, and a fully deployed configuration in which the sheath is fully retracted to expose the distal and proximal bodies.

In one embodiment, the device is configured for adjustment between a delivery configuration in which the distal and proximal bodies are spaced apart and contracted, a first deployment configuration in which the energy delivery element and sensor are deployed, a second deployment configuration in which the distal body is deployed, a third deployment configuration in which the proximal body is deployed, a fourth deployment configuration in which the distal and proximal bodies are adjusted to the axially adjacent configuration and the brake mechanism is actuated, and a final deployment configuration in which the sensor and energy delivery element is withdrawn (i.e. retracted into the catheter member) and the elongated catheter body is detached from the occlusion body.

In one embodiment, the device comprises a control handle disposed on a proximal end of the elongated catheter member and including a control for remotely actuating deployment of the distal and proximal bodies, and a control for remotely adjusting the axial spacing of the distal and proximal bodies.

In one embodiment, the distal body comprises an anchor configured to anchor the distal body to the wall of the left atrial appendage.

In one embodiment, one or both facing sides of the radially expansible bodies, ideally a periphery of the or each facing side, include an anchor configured to anchor tissue gathered between the radially expansible bodies. The anchor may be a barb or a hook.

In one embodiment, the energy delivery element is disposed between the radially expansible bodies. In one embodiment, the energy delivery element comprises one or a plurality of energy delivery elements which extend radially outwardly towards the surrounding tissue.

In one embodiment, a facing side of at least one, and preferably both, of the radially expansible bodies includes an energy shielding element, and in particular an electromagnetic shielding element. The purpose of the shielding element is to enhance the directionality of energy from the energy delivery element, and limit the dispersion of energy to between the radially expansible bodies providing protection to areas of tissue outside the radially expansible bodies.

In one embodiment, a periphery of the facing sides of the radially expansible bodies include an electromagnetic reflective element.

In one embodiment, the energy delivery element is disposed on the proximal and distal radially expansible bodies, wherein one of the bodies is an RF cathode and the other of the bodies is an RF anode In one embodiment, the body lumen is the left atrial appendage (LAA), and in which the elongated catheter member comprises a positioning radially expansible body disposed proximally of the radially expansible element, and is configured for adjustment between a contracted orientation suitable for transluminal delivery and a deployed orientation configured to occlude the LAA opening.

In one embodiment, the positioning radially expansible body is a balloon, whereby inflation or deflation of the balloon causes adjustment of the depth of the occlusion apparatus in the LAA.

In one embodiment, the device comprises a cooling element disposed distally of the radially expansible element. In one embodiment the cooling element is a balloon, which can be inflated with cooled fluid, or example a cryogenic fluid. In one embodiment, the cooling element is disposed on an end of a catheter member, which is adjustable axially relative to the radially expansible element. This allows the cooling element to be moved into the proximity of the phrenic nerve, where the cooling effect protects the phrenic nerve and surrounding tissue from damage caused by the energy delivery element.

In one embodiment, a circumference and/or side of the radially expansible element comprises bristles. In one embodiment, the circumferential bristles extend radially and the side bristles extend axially.

In one embodiment, the radially expansible element comprises a circumferential inflatable cuff. In one embodiment, the cuff comprises an energy delivery element. In one embodiment, the cuff comprises a sensor.

In one embodiment, the sensor is configured to pace the tissue of the LAA.

In one embodiment, the occlusion apparatus comprises a telemetry module operably connected to the sensor and configured to wirelessly relay sensing data to a remote base station. In one embodiment, the occlusion apparatus comprises a piezo-electric energy harvesting module operably connected to the sensor and telemetry module, optionally via a battery. In one embodiment, the sensor is configured to pace the tissue of the LAA. In one embodiment, the piezo-electric energy harvesting module is disposed on a proximal side of the occlusion body and exposed to pressure waves generated in the left atrium.

In another aspect, the invention provides a system for heating tissue comprising:
  a device of the invention having a blood flow sensor disposed on or distally of the radially expansible body and optionally a temperature sensor disposed on the radially expansible body;
  an energy source operably connected to the energy delivery element through the elongated catheter member; and
  a processor operably connected to the energy source, the blood flow sensor and optionally the temperature sensor, and configured to control the delivery of energy from the energy source to the energy delivery element in response to measurement signals received from the or each sensor.

In another aspect, the invention provides a system for heating tissue comprising:
- a device of the invention having a blood flow sensor disposed on or distally of the radially expansible body and optionally a temperature sensor disposed on the radially expansible body;
- energy control means for controlling the delivery of energy from an energy source through the elongated catheter member to the energy delivery element; and
- a processor operably connected to the energy control means and the sensor, and configured to control the delivery of energy from the energy source to the energy delivery element in response to measurement signals received from the or each sensor.

In one embodiment, the processor is configured to receive a signal from the blood flow sensor and provide an output based on the received signal relating to the blood flow or atrial fibrillation.

In one embodiment, the processor is configured to control the energy (heating) cycle duration in response to measurement signals received from temperature sensor. Thus, the processor can control the heating of the tissue to maintain the heating of the tissue at a suitable ablation temperature, for example between 45 and 70 degrees Celsius.

In one embodiment, the processor is configured to control the number of energy (heating) cycles in response to measurement signals received from the blood flow sensor. Thus, the processor can control the duration of the heating of the tissue to maintain the heating until the measurement signals from the blood flow sensor indicate that blood flow to the wall of the body lumen (i.e. the wall of the LAA) distal of the radially expansible element has been permanently disrupted.

In one embodiment, the energy source is an electromagnetic energy source (for example a microwave or RF energy source). In one embodiment, the energy source is configured to deliver electromagnetic energy in the range of 0.1 Watt to 60 Watts.

In one embodiment, the system comprises a pump configured to deliver or withdraw a fluid from the body lumen distally of the radially expansible member.

In another aspect, the invention provides a method of narrowing, occluding or devascularisation of a body lumen comprising the steps of percutaneously delivering a device of the invention to the body lumen, in which the radially expansible element is in a contracted orientation, deploying the radially expansible element, delivering energy to the energy delivery element to heat the surrounding wall of the body lumen, sensing blood flow in the wall of the body lumen distal of the radially expansible element either intermittently or continuously during the heating step, and maintaining the heating until the measurement signals received from the blood flow sensor indicate sufficient disruption of blood flow (i.e. partial or complete) in the wall of the body lumen distal of the radially expansible body.

In another aspect, the invention provides a method of narrowing, occluding or devascularisation of a body lumen that employs a delivery device of the invention having a delivery catheter member and an occlusion apparatus comprising distal radially expansible body and a proximal radially expansible body, the method comprising the steps of percutaneously delivering the device to the body lumen, in which the radially expansible bodies are in a contracted orientation, deploying the distal and proximal radially expansible elements in a spaced apart orientation, axially adjusting the radially expansible bodies into an axially adjacent position whereby a portion of the wall of the body lumen is gathered between the bodies, and delivering energy to the energy delivery element to heat the surrounding wall of the body lumen including the portion of the wall of the body lumen gathered between the bodies.

In one embodiment, the method includes a further step of detaching the radially expansible element from the catheter member after the heating step and retracting the catheter member, energy delivery element and optionally sensor from the subject leaving the radially expansible element part of the occlusion apparatus in-situ in the body lumen. In one embodiment, the energy delivery element and sensor are retracted into the catheter member, and the catheter member is retracted with the energy delivery element and sensor disposed in the catheter member.

In another embodiment, the method includes a further step of detaching the occlusion apparatus from the catheter member after the heating step and retracting the catheter member from the subject leaving the occlusion apparatus in-situ in the body lumen. In one embodiment, the occlusion apparatus comprises a telemetry module operably connected to the sensor and configured to wirelessly relay sensing data to a remote base station. In one embodiment, the occlusion apparatus comprises a piezo-electric energy harvesting module operably connected to the sensor and telemetry module, optionally via a battery. In one embodiment, the sensor is configured to pace the tissue of the LAA.

The heating step typically involves a plurality of heating cycles, and may provide continuous or intermittent heating. The duration and/or length of the heating cycles may be adjusted.

In one embodiment, the device of the invention comprises a temperature sensor configured to detect the temperature of the surrounding tissue being heated (for example, disposed on or distal of the radially expansible body), in which the method includes additional steps of sensing the temperature of the surrounding wall of the body lumen, and controlling the heating step (for example by controlling the duration of the heating cycles) to keep the temperature of the surrounding wall of the body lumen at a suitable temperature, for example 45 to 70 degrees Celsius.

In one embodiment, the device of the invention comprises proximal and distal radially expansible bodies, wherein deployment of the radially expansible element comprises deployment of the distal radially expansible body, and then deployment of the proximal radially expansible body.

In one embodiment, the device of the invention comprises proximal and distal radially expansible bodies, in which the method includes a step prior to or during the heating step of axially adjusting the radially expansible bodies into an axially adjacent position whereby a portion of the wall of the body lumen is gathered between the bodies and heated.

In one embodiment, the method is a method of occluding or devascularisation of the LAA.

In one embodiment, the method is a method of treatment or prevention of an arrhythmia or atrial fibrillation, prevention of a thrombotic event, or treatment or prevention of ischaemia or a hypertensive disorder, in a subject. In one embodiment, the subject has a LAA.

In one embodiment, the body lumen is a heart valve opening, for example the aortic valve opening, and wherein the method is a method of narrowing the (aortic) valve opening, for example prior to (aortic) valve replacement. The invention also relates to a method of (aortic) valve replacement comprising an initial step of narrowing the (aortic) valve opening by a method of the invention, or by using a device or system of the invention. Thus, the method of the invention may be employed to narrow the aortic valve opening prior to trans aortic valve implantation.

Other aspects and preferred embodiments of the invention are defined and described in the other claims set out below.

BRIEF DESCRIPTION OF THE FIGURES

FIG. 9A shows the device of the invention in a delivery configuration being delivered transluminally into the left atrium of the heart and into the LAA;

FIG. 9B shows the deployment of the occlusion apparatus in the LAA blocking the LAA;

FIG. 9C shows the further deployment of the sensor distally to the end of the LAA;

FIGS. 9D and 9E shows the contraction of the energy delivering radially expansible body and retraction of the sensor to a retraction configuration;

FIG. 9F shows the energy delivery element and sensor fully retracted into the catheter member, and the catheter member detached from the radially expansible element, leaving the radially expansible element in-situ in the body lumen;

FIGS. 14A and 14B are an end view and side view, respectively, of the cover that covers the proximal side of the radially expansible element, and showing the self-closing aperture (flap); and FIGS. 15A and 15B, and 16A and 16B, show how the catheter member projects through the self-closing aperture in the cover.

DETAILED DESCRIPTION OF THE INVENTION

Figure 1:
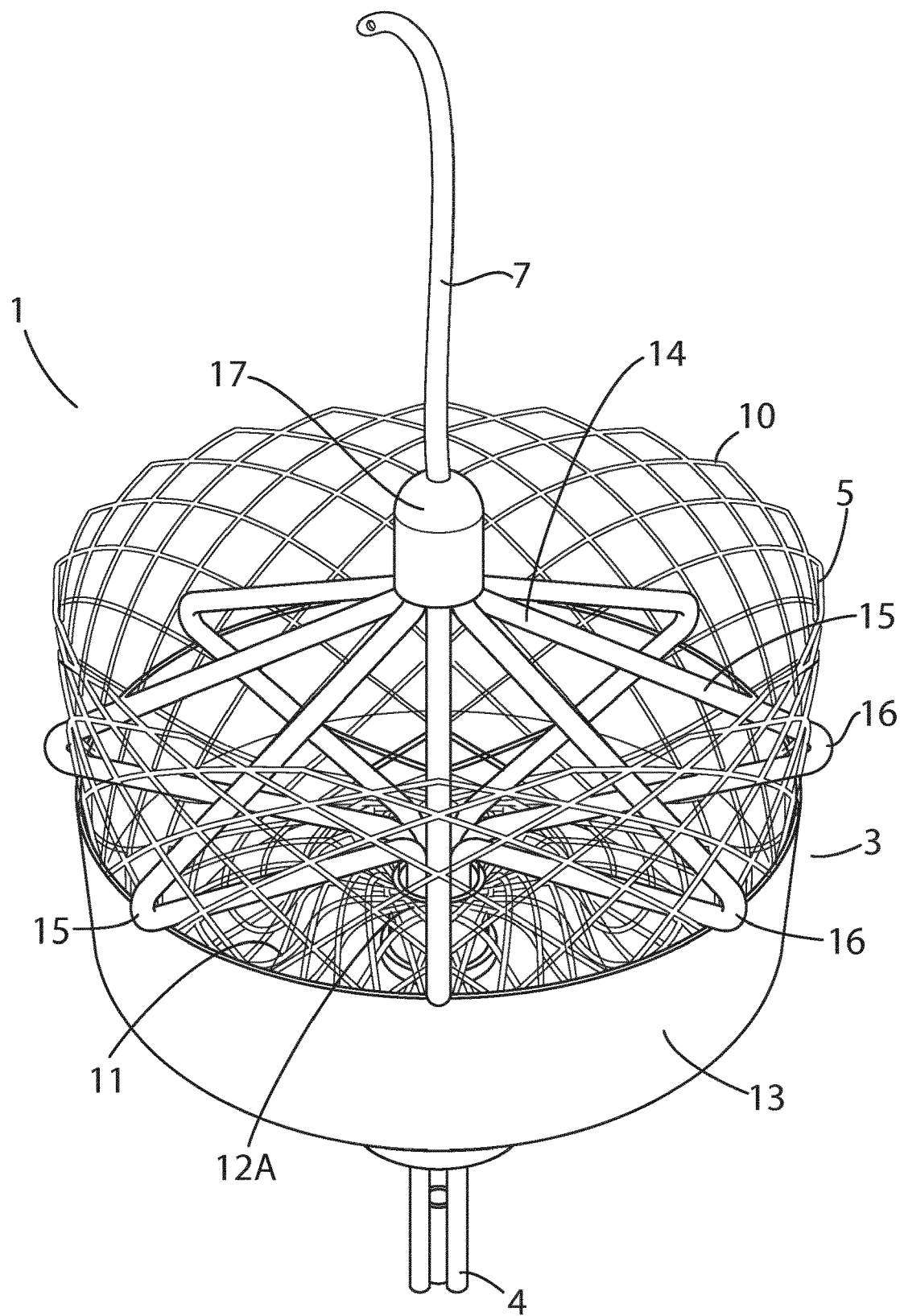
FIG. 1 is a perspective view of a device of the invention, having an energy delivery element in the form of a radially expansible cage.

All publications, patents, patent applications and other references mentioned herein are hereby incorporated by reference in their entireties for all purposes as if each individual publication, patent or patent application were specifically and individually indicated to be incorporated by reference and the content thereof recited in full.

DEFINITIONS AND GENERAL PREFERENCES

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s) (for example, the reduction in accumulation of pathological levels of lysosomal enzymes). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

"Implantable occlusion apparatus" means an apparatus configured for implantation in a body lumen, especially implantation in the heart at least partially within the left atrial appendage, and upon actuation to occlude the body lumen resulting in partial or complete devascularisation of the body lumen. The occlusion apparatus is detachably connected to a delivery catheter which delivers the occlusion apparatus to the target site, and typically remains attached during occlusion, sensing and energy delivery treatments and is detached after the energy delivery treatment and removed from the body leaving the occlusion apparatus (or the radially expansible element part of the occlusion apparatus) implanted in the body lumen. Occlusion may be complete occlusion (closing) of the body lumen or partial occlusion (narrowing of the body lumen or near complete occlusion).

"Body lumen" means a cavity in the body, and may be an elongated cavity such as a vessel (i.e. an artery, vein, lymph vessel, urethra, ureter, sinus, auditory canal, nasal cavity, bronchus) or an annular space in the heart such as the left atrial appendage, left ventricular outflow tract, the aortic valve, the mitral valve, mitral valve continuity, or heart valve or valve opening.

"Detachably attached" means that the device is configured such that the occlusion apparatus is attached to the elongated delivery catheter during delivery and can be released after deployment and treatment whereby the occlusion apparatus, or just the radially expansible element part of the occlusion apparatus, is implanted in the heart and the elongated delivery catheter can be withdrawn leaving the occlusion apparatus (or the radially expansible element) in-situ. Typically, the device includes a control mechanism for remotely detaching the occlusion apparatus or radially expansible element from the elongated catheter member. Typically, an actuation switch for the control mechanism is disposed on the control handle.

"Elongated catheter member" means an elongated body having a distal end that is operably and detachably connected to the occlusion apparatus. In one embodiment, the catheter member comprises a control arm (for example a tubular member) operably connected to the proximal body, and a control arm operably connected to the distal body. The control arm may take any forms, for example, a rod, wire, or tubular member. In one embodiment, both control arms are disposed within a lumen in the catheter member. In one embodiment, the control arm for the proximal body is a tubular member, and the control arm for the distal body is disposed within a lumen in the tubular member. In one embodiment, the distal body control arm is adapted for retraction relative to the proximal body control arm. In one embodiment, the catheter comprises an external sheath that is axially adjustable between a first position in which it covers the distal and proximal body, a second position in which the distal body is exposed and the proximal body is covered, and a third position in which the distal and proximal bodies are exposed. Thus, when the distal and proximal body are self-expansible, the sheath can be used to deploy the bodies individually and sequentially.

"Transluminal delivery" means delivery of the occlusion apparatus to a target site (for example the heart) heart through a body lumen, for example delivery through an artery or vein. In one embodiment, the device of the invention is advanced through an artery or vein to deliver the occlusion apparatus to the left atrium of the heart and at least partially in the LAA. In one embodiment, the device is delivered such that the distal body is disposed within the LAA and the proximal body is disposed in the left atrium just outside the LAA. In one embodiment, the device is delivered such that the distal body is disposed within the LAA and the proximal body is disposed in the left atrium abutting a mouth of the LAA. In one embodiment, the device is delivered such that both the distal body and proximal body are disposed within the LAA.

"Body" as applied to distal body or proximal body means a body that is expansible from a contracted delivery configuration to an expanded deployed configuration. The body may take many forms, for example a wireframe structure formed from a braided or meshed material. Examples of expandable wireframe structures suitable for transluminal delivery are known in the literature and described in, for example, WO01/87168, U.S. Pat. No. 6,652,548, US2004/219028, U.S. Pat. Nos. 6,454,775, 4,909,789, 5,573,530, WO2013/109756. Other forms of bodies suitable for use with the present invention include plate or saucer shaped scaffolds, or inflatable balloons, or stents. In one embodiment, the body is formed from a metal, for example a shape-memory metal such as nitinol. The body may have any shape suitable for the purpose of the invention, for example discoid or spheroid. In one embodiment, the body comprises a tissue ablation device. In one embodiment, the ablation device comprises an array of electrical components. In one embodiment, the array of electrical components are configured to deliver ablative energy in a specific pattern while mapping temperature. In one embodiment, the array of electrical components are configured for pacing the cardiac tissue for confirmation of ablation and disruption of chaotic signalling from the LAA. In one embodiment, a distal face of the radially expansible body comprises a covering configured to promote epithelial cell proliferation. In one embodiment, the body comprises a stepped radial force stiffness profile from distal to proximal device. In one embodiment, the body comprises a metal mesh cage scaffold. In one embodiment, a coupling between the body and the catheter member is located distally to the left atrial facing side of the body. In one embodiment, the body in a deployed configuration has a radial diameter at least 10% greater than the radial diameter of the left atrial appendage at a point of deployment. In one embodiment, the furthermost distal body is configured to be atraumatic to cardiac tissue. In one embodiment, the body covering is configured to self-close on retraction of the delivery component (i.e. catheter member). In one embodiment, the body comprises a braided mesh scaffold that in one embodiment is conducive to collagen infiltration on thermal energy delivery to promote increased anti migration resistance. In one embodiment, the array of electrodes generate an electrical map or profile of the ablation zone and the surrounding tissue electrical impedance measurements to characterise the electrical properties of the tissue, wherein the characterisation is optionally used as a measurement and confirmation of ablation effectiveness.

"Radially expansible element" means a body forming part of the occlusion apparatus that is configured for radial expansion from a contracted delivery configuration to a radially expanded deployed configuration. In one embodiment, the radially expansible element is a single body having a distal end and a proximal end. In another embodiment, the radially expansible element comprises a distal radially expansible body and a proximal radially expansible body.

"Distal radially expansible body" means a body forming part of the occlusion apparatus that is disposed on the device distally of the proximal body. In one embodiment, the distal body is configured such that upon deployment into the expanded configuration, it has a radial dimension that is greater than a radial dimension of the body lumen (i.e. the LAA) at the point of deployment. This ensures that the distal body upon deployment bears against the wall of the body lumen, thereby internally gripping the wall. In one embodiment, the radial dimension of the distal body is at least 10%, 15%, 20%, 25%, 30%, 35% or 40% greater than a radial dimension of the body lumen. In one embodiment, the proximal body is configured to deliver energy to the body lumen, ideally the ostial pathway of the LAA. In one embodiment, the energy is RF energy or heat. In one embodiment, the proximal body comprises an energy delivering electrical component for example an electrode or an array of electrodes. In one embodiment, the proximal body is a cryoballoon.

"Proximal body" means a body forming part of the occlusion apparatus that is disposed on the device proximally of the distal body. In one embodiment, the distal body is configured such that upon deployment into the expanded configuration, it has a radial dimension that is greater than a radial dimension of the mouth of the LAA at the point of deployment. This ensures that the proximal body upon deployment abuts a mouth of the LAA, thereby anchoring the occlusion in body in position such that retraction of the distal body causes gathering and compression of the wall of the LAA between the distal and proximal bodies. In one embodiment, the proximal body is configured to create a seal between the LAA and the LA.

"Radially expansible" means expansible from a contracted configuration suitable for delivery to a deployed expanded position. Typically, the bodies are radially expansible about a longitudinal axis of the device. One or both of the bodies may be self-expansible.

In another embodiment, the bodies are not self-expansible, but are configured for manual deployment. Expansible bodies configured for manual expansion are described in PCT/IE2014/000005.

"Axially spaced-apart" means that the distal and proximal bodies are spaced apart along a longitudinal axis of the device such that when the proximal body is positioned at a mouth of the LAA, the distal body will be disposed within the LAA. In one embodiment, the axial spacing during delivery is from 2-10 mcm, preferably 3-5 mcm.

"Axially adjacent" means closer together than axially spaced-apart, and typically means the bodies being sufficiency close together to effect devascularisation of the tissue compressed between the distal and proximal bodies. In one embodiment, the spacing between the distal and proximal bodies in the axially adjacent orientation is from 1-5 mm, preferably 1-3 mm.

"Disposed proximally of a mouth of the left atrial appendage" as applied to the proximal body means that the proximal body is disposed within the left atrium and outside of the LAA, typically adjacent a mouth of the LAA, and ideally abutting a mouth of the LAA.

"Invaginates into a wall of the left atrial appendage" means that the periphery of the distal body upon deployment beds into the lateral wall of the LAA at the point of deployment. In one embodiment, the point of deployment of the distal body is disposed between one-third and two-thirds along the LAA. In one embodiment, the point of deployment of the distal body is disposed approximately half-way along the LAA.

"Gathers and compresses the wall of the left atrial appendage" refers to the process where the distal and proximal bodies gather and compress part of the lateral wall of the body lumen (i.e. the LAA).

"Brake mechanism" refers to a mechanism that when actuated locks the position of the distal body relative to the proximal body. The purpose of the mechanism is to the fix the axial positions of the distal and proximal bodies when in the active, axially adjacent, orientation, so that when the delivery catheter is detached from the occlusion body and withdrawn from the patient, the distal and proximal bodies will remain in the active clamping orientation. In one embodiment, the distal and proximal clamping bodies are operably connected by means of a braking mechanism. A number of embodiments of braking mechanisms are described below with reference to FIGS. 23 to 26. In one embodiment, the distal and proximal bodies are connected by a threaded arrangement (FIG. 23) whereby rotation of one of the bodies relative to the other body results adjusts the axial spacing of the bodies and maintains the bodies in a fixed position. In another embodiment, the bodies are connected by a snap-fit arrangement (FIG. 24), whereby axial adjustment of the bodies into a pre-set axially adjacent position results in the bodies snapping together into a locked position. In another embodiment, the bodies are connected by a ratchet arrangement (FIG. 25), providing a number of different pre-set axially adjacent positions, allowing a surgeon increase the level of compression of the wall of the LAA in an iterative manner until the desired level of compression has been achieved. Other braking mechanisms are also envisaged and will be apparent to a person skilled in the art.

"Cover" typically means a layer covering the proximal side of radially expansible element. It is intended to prevent blood flow past the occlusion apparatus into the LAA. It may be formed from a woven mesh material, and may include a re-closable aperture, for example an overlapping flap of material. When the device has two bodies, the cover may be disposed on a proximal or distal side of the proximal body. When the radially expansible body is a single body, the cover is generally disposed on a proximal side of the body. In some embodiment, the connecting hub is disposed in a recess between the cover and the concave proximal face of the radially expansible body.

"Covering/cover configured to promote epithelial cell proliferation" means a material that is use promotes epithelialisation of the distal or proximal body. In one embodiment, the covering is a membrane that comprises agents that promote epithelial cell proliferation.

Examples include growth factors such as fibroblast growth factor, transforming growth factor, epidermal growth factor and platelet derived growth factor, cells such as endothelial cells or endothelial progenitor cells, and biological material such as tissue or tissue components. Examples of tissue components include endothelial tissue, extracellular matrix, sub-mucosa, dura mater, pericardium, endocardium, serosa, peritoneum, and basement membrane tissue. In one embodiment, the covering is porous. In one embodiment, the covering is a biocompatible scaffold formed from biological material. In one embodiment, the covering is a porous scaffold formed from a biological material such as collagen. In one embodiment, the covering is a lyophilised scaffold.

"Retractable delivery sheath" means a sheath configured to cover the distal and proximal bodies during transluminal delivery and retraction during deployment to expose the distal and proximal bodies individually and sequentially. A retractable sheath is employed when the distal or proximal body (or both) are self-expansible.

"Control handle" means an apparatus disposed on a proximal end of the elongated catheter and operably connected to the occlusion body for remote actuation of the occlusion body, for example axial movement of the distal body, deployment of the distal and proximal bodies, and detachment of the occlusion body from the elongated catheter member.

"Anchor" as applied to the distal or proximal body, means a projection, typically on a periphery of the body, configured to project into the wall of the LAA. Examples of suitable anchors include hooks or barbs. Generally, the anchor comprises a plurality of individual anchors, for example disposed around a periphery of the distal or proximal body.

"Sensor" means an electrical sensor configured to detect an environmental parameter within or proximal of the LAA, for example blood flow, electrical signal activity, pressure, impedance, moisture or the like. The sensor may include an emission sensor and a detection sensor that are suitably spaced apart. In one embodiment, the sensor is an electrode. In one embodiment, the sensor is configured to detect fluid flow. In one embodiment, the sensor is configured to detect electrical conductivity. In one embodiment, the sensor is configured to detect electrical impedance. In one embodiment, the sensor is configured to detect an acoustic signal. In one embodiment, the sensor is configured to detect an optical signal typically indicative of changes in blood flow in the surrounding tissue. In one embodiment, the sensor is configured to detect stretch. In one embodiment, the sensor is configured to detect moisture. In one embodiment, the sensor is configured for wireless transmission of a detected signal to a processor. The sensor may be employed in real time during the method of the invention to allow a surgeon determine when the LAA is sufficiently occluded, for example determining blood flow or electrical activity within the LAA. Examples suitable sensor include optical sensors, radio frequency sensors, microwave sensors, sensors based on lower frequency electromagnetic waves (i.e. from DC to RF), radiofrequency waves (from RF to MW) and microwave sensors (GHz). In one embodiment, the device of the invention is configured for axial movement of the sensor relative to the radially expansible body. In one embodiment, the device of the invention is configured for rotational movement of the sensor, typically about a longitudinal axis of the device. This helps positioning of the sensor, and helps achieve full circumferential sensing.

"Optical sensor" means a sensor suitable for detecting changes in blood flow in tissue, and which generally involves directing light at the tissue and measuring reflected/transmitted light. These sensors are particularly sensitive for detecting changes in blood flow in adjacent tissue, and therefore suitable for detecting devascularisation of tissue such as the LAA. Examples include optical probes using pulse oximetry, photoplasmography, near-infrared spectroscopy, Contrast enhanced ultrasonography, diffuse correlation spectroscopy (DCS), transmittance or reflectance sensors, LED RGB, laser doppler flowometry, diffuse reflectance, fluorescence/autofluorescence, Near Infrared (NIR) imaging, diffuse correlation spectroscopy, and optical coherence tomography. An example of a photopeasmography sensor is a device that passes two wavelengths of light through the tissue to a photodetector which measures the changing absorbance at each of the wavelengths, allowing it to determine the absorbances due to the pulsing arterial blood alone, excluding venous blood, muscle, fat etc.). Photoplesmography measures change in volume of a tissue caused by a heart beat which is detected by illuminating the tissue with the light from a single LED and then measuring the amount of light either reflected to a photodiode.

"Energy delivering element" refers to a device configured to receive energy and direct the energy to the tissue, and ideally convert the energy to heat to heat the tissue causing collagen denaturation (tissue ablation). Tissue ablation devices are known to the skilled person, and operate on the basis of emitting thermal energy (heat or cold), microwave energy, radiofrequency energy, other types of energy suitable for ablation of tissue, or chemicals configured to ablate tissue. Tissue ablation devices are sold by ANGIODYNAMICS, including the STARBURST radiofrequency ablation systems, and ACCULIS microwave ABLATION SYSTEMS. Examples of tissue ablating chemicals include alcohol, heated saline, heated water. Typically, the liquid is heated to at least 45° C., i.e. 45-60° C. In one embodiment, the tissue ablation device comprises an array of electrodes or electrical components typically configured to deliver heat to adjacent tissue. (alcohol, heated saline, heated water) In one embodiment, one or more of the electrodes comprises at least one or two thermocouples in electrical communication with the electrode. In one embodiment, one or more of the electrodes are configured to deliver RF or microwave energy. In one embodiment, the device of the invention is configured for axial movement of the energy delivery element relative to the radially expansible body. In one embodiment, energy delivery element comprises a radially expansible body. In one embodiment, the device of the invention is configured for rotational movement of the energy delivery element, typically about a longitudinal axis of the device. This helps positioning of the energy delivering element, and helps achieve full circumferential tissue ablation.

"Atrial fibrillation" or "AF" is a common cardiac rhythm disorder affecting an estimated 6 million patients in the United States alone. AF is the second leading cause of stroke in the United States and may account for nearly one-third of strokes in the elderly. In greater than 90% of cases where a blood clot (thrombus) is found in the AF patient, the clot develops in the left atrial appendage (LAA) of the heart. The irregular heart beat in AF causes blood to pool in the left atrial appendage, because clotting occurs when blood is stagnant, clots or thrombi may form in the LAA. These blood clots may dislodge from the left atrial appendage and may enter the cranial circulation causing a stroke, the coronary circulation causing a myocardial infarction, the peripheral circulation causing limb ischemia, as well as other vascular beds. The term includes all forms of atrial fibrillation, including paroxysmal (intermittent) AF and persistent and longstanding persistent AF (PLPAF).

"Ischaemic event" refers to a restriction in blood supply to a body organ or tissue, resulting in a shortage of oxygen and glucose supply to the affected organ or tissue. The term includes stroke, a blockage of blood supply to a part of the brain caused by a blood clot blocking the blood supply to the brain and the resultant damage to the affected part of the brain, and transient ischaemic events (TIA's), also known as "mini-strokes", which are similar to strokes but are transient in nature and generally do not cause lasting damage to the brain. When the restriction in blood supply occurs in the coronary arteries, the ischaemic event is known as a myocardial infarction (MI) or heart attack.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Referring to FIGS. 1 to 4, there is illustrated a device for occlusion of a body lumen, in this case the left atrial appendage (LAA) of the heart 2, indicated generally by the reference numeral 1. The device 1 comprising an implantable occlusion apparatus 3 operably attached to an elongated catheter member 4 configured for transluminal delivery and deployment of the occlusion apparatus in the body lumen. The occlusion apparatus 3 comprises a radially expansible element 5 detachably attached to the elongated catheter member 4, and adjustable between a contracted orientation suitable for transluminal delivery and a deployed orientation configured to occlude the body lumen as shown in FIG. 1. The occlusion apparatus also comprises an energy delivery element 6 configured to deliver energy to surrounding tissue to heat the tissue, and a sensor 7 configured to detect a parameter of the wall of the body lumen. The energy delivery element 6 and sensor 7 are axially movable independently of the radially expansible element 5 enabling the energy delivery element and sensor to be transluminally retracted leaving the radially expansible element in-situ occluding the body lumen (FIGS. 9D to 9F).

In more detail, the radially expansible element 5 is a wire mesh cage having an open cylindrical distal end 10, a closed proximal end 11 having a partially toroidal shape with a recessed central core 12A and connecting hub 12B defining an aperture, and a blood-impermeable cover 13 covering the proximal end which functions to prevent blood flow into the LAA once the occlusion apparatus has been deployed. The radially expansible element 5 is formed from a shape memory material and is configured for adjustment from a contracted delivery configuration (FIG. 9A) to an expanded deployed configuration shown in FIG. 1. A delivery sheath configured to cover the radially expansible element 5 and maintain it in a contracted delivery configuration during transluminal delivery is described in more detail below.

Figure 2:
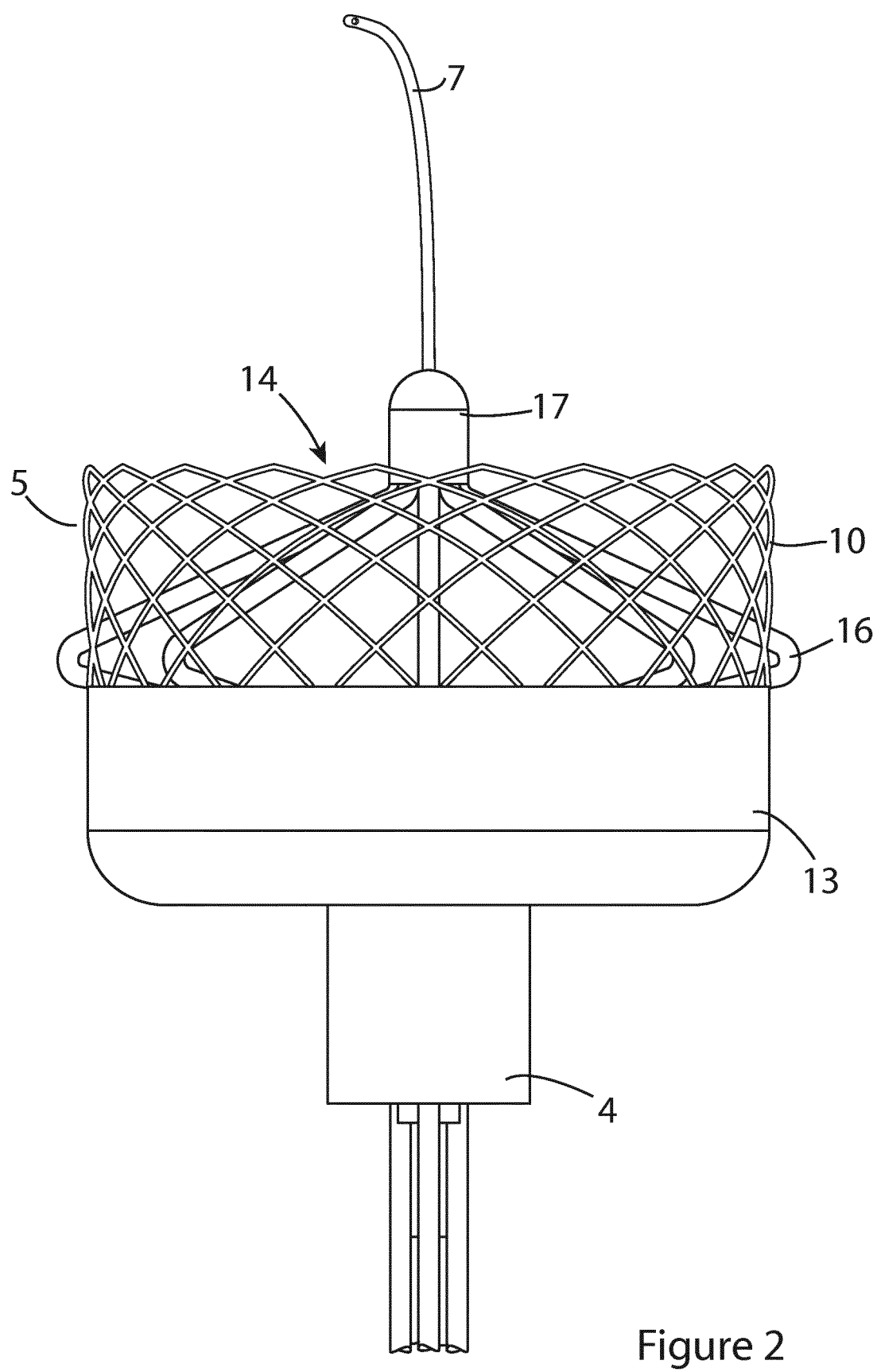
FIG. 2 is a side elevational view of the device of FIG. 1.
Figure 3:
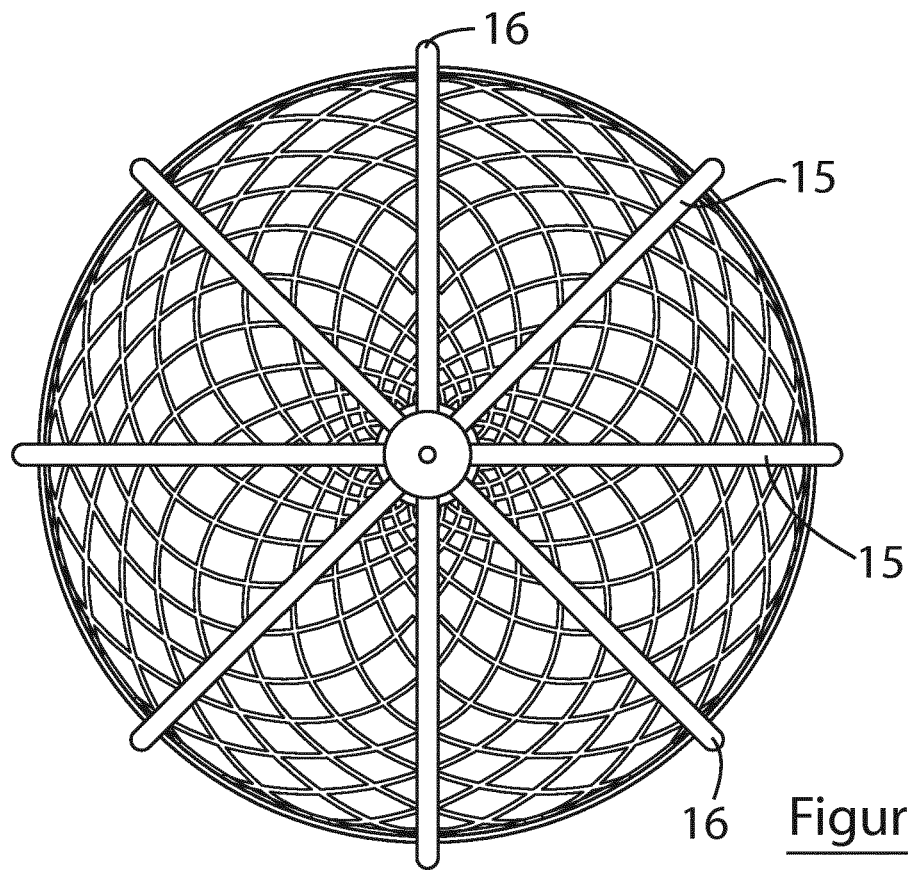
FIGS. 3 and 4 are top and bottom plan view of the device of FIG. 1, respectively.
Figure 4:
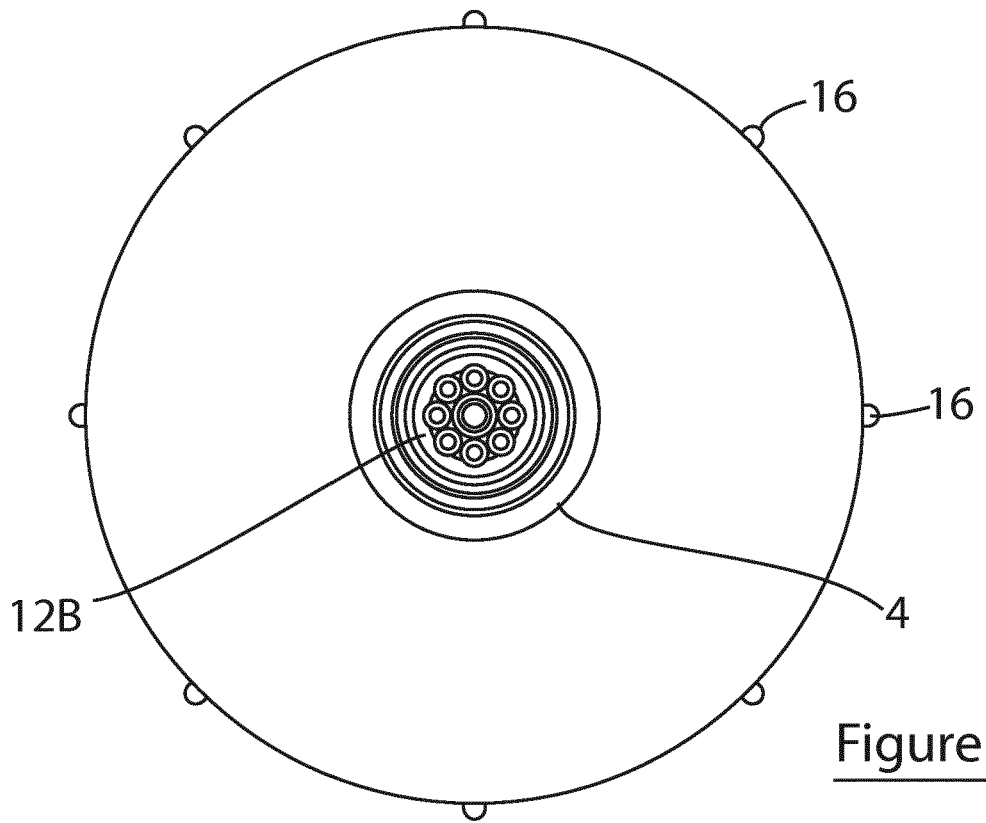

The energy delivery element 6 is also provided in the form of a radially expansible body 14 and comprises a plurality of V-shaped tissue ablation elements 15 interconnected at their ends and arranged radially around a longitudinal axis of the device, and is configured for radial expansion from a contracted delivery configuration (See FIG. 9A) to an expanded deployed configuration shown in FIG. 1. The radially expansible body 14 is disposed within the radially expansible element 5 and dimensioned such that when it is deployed the elbows 16 of the V-shaped elements 15 project through the mesh of the radially expansible element 5 as shown in FIGS. 2 and 4, so that in use they come into contact with the tissue surrounding the radially expansible element. The distal end of the radially expansible body 14 comprises a connecting hub 17. The sensor 7, in this case an optical sensor, projects axially through the radially expansible element 5 and through the connecting hub 17 and in configured for axial extension distally of the radially expansible element as shown in FIG. 1 (during treatment), and axial retraction proximal of the radially expansible element 5 and into the catheter member (during delivery and retraction).

Although not illustrated, the energy delivering radially expansible body 15 includes control arms which are actuated during use to deploy and retract the body, including a distal control arm attached to a distal end of the body 14 and a proximal control arm attached to a proximal end of the body, such that relative axial movement of the arms causes the body to expand or contract.

Figure 5:
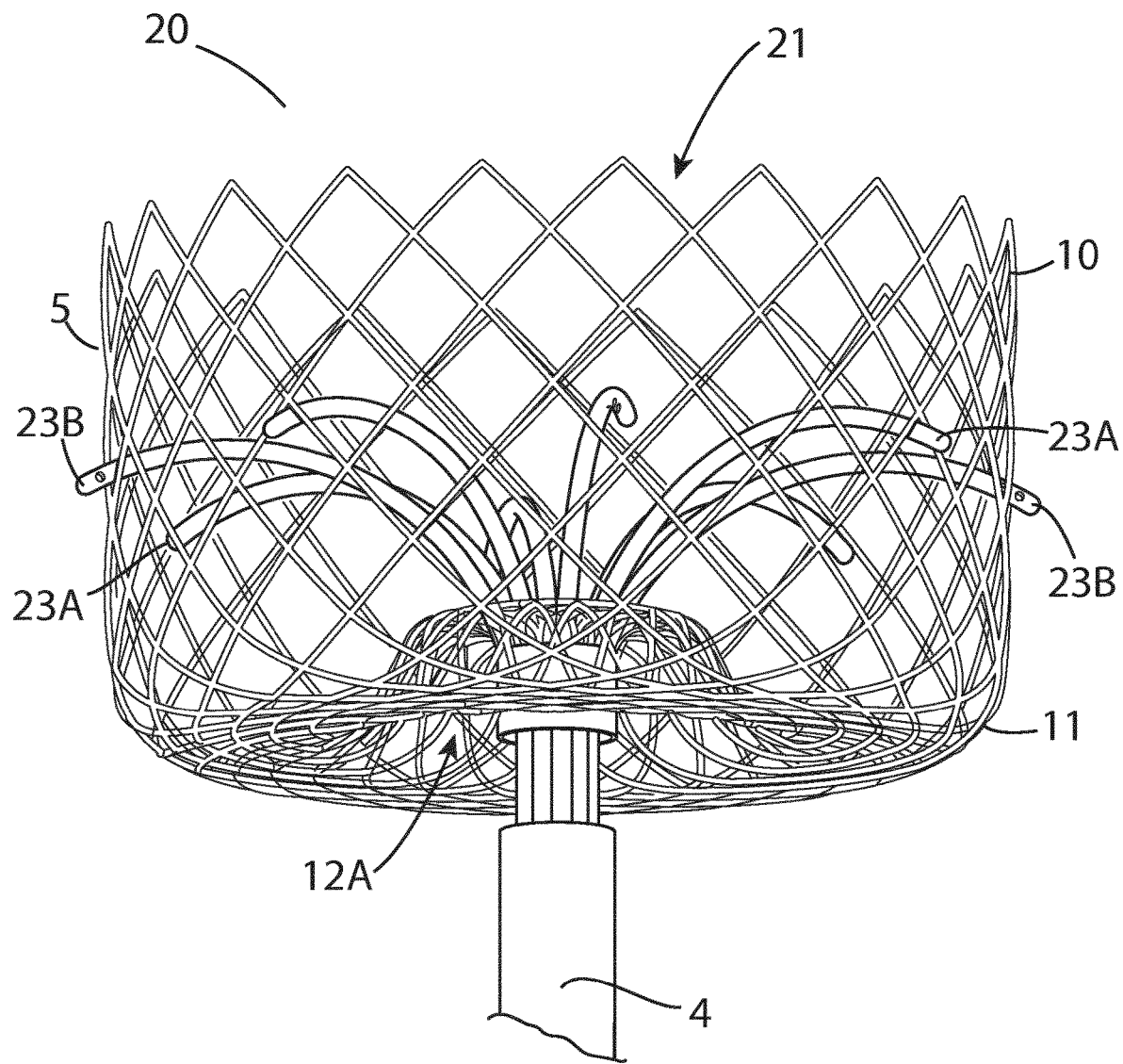
FIG. 5 is a perspective view of an alternative embodiment of a device of the invention, having an energy delivery element in a "palm tree" form.
Figure 6:
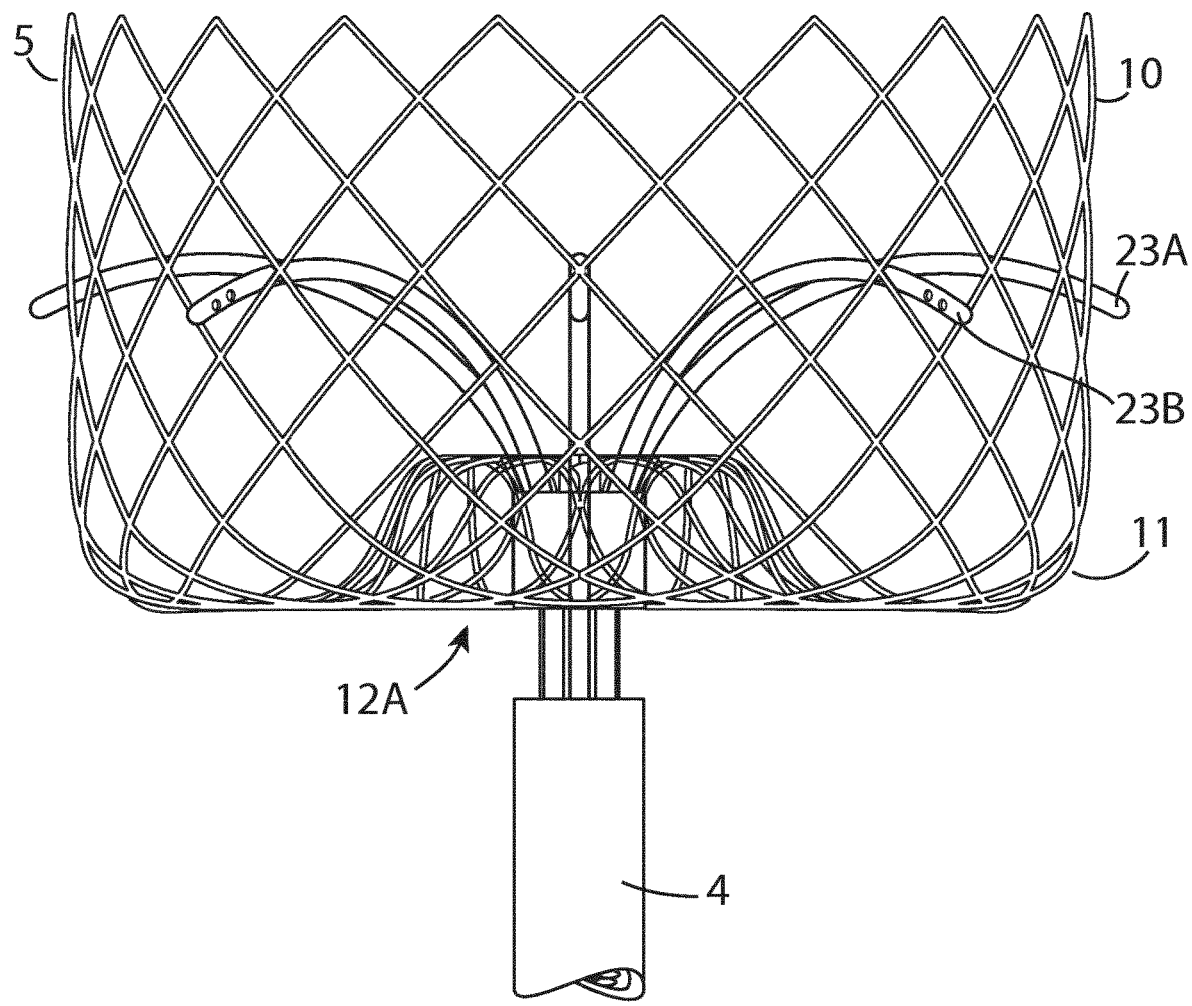
FIG. 6 is a side elevational view of the device of FIG. 5.
Figure 7:
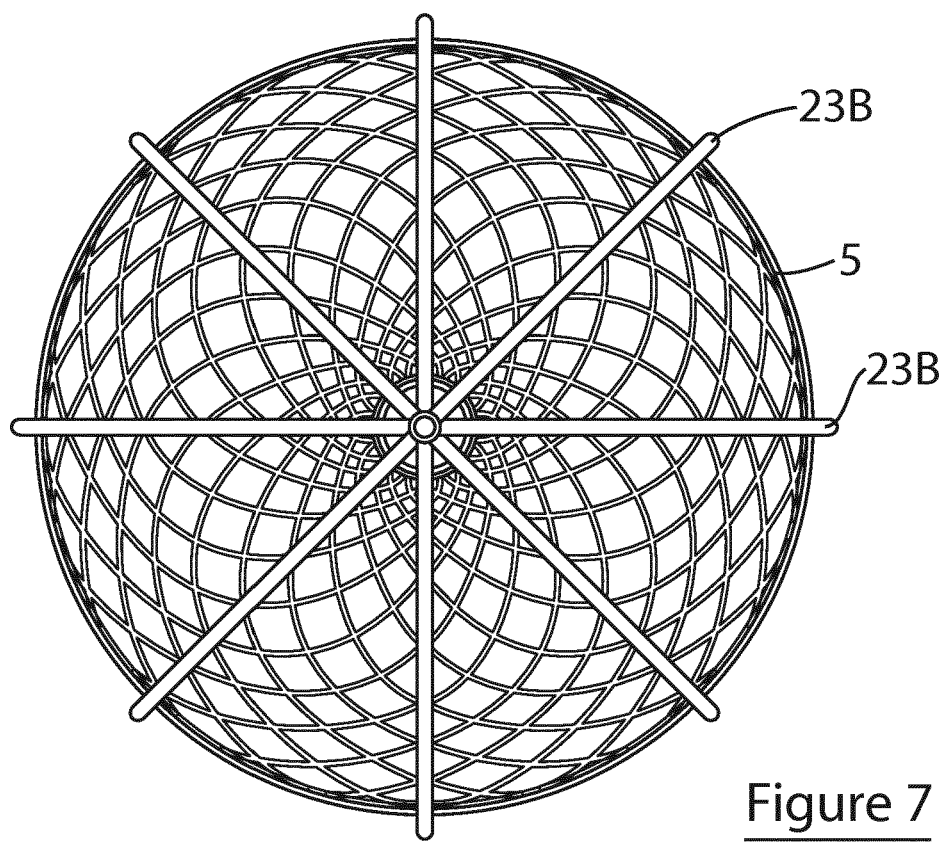
FIGS. 7 and 8 are top and bottom plan view of the device of FIG. 5, respectively.
Figure 8:
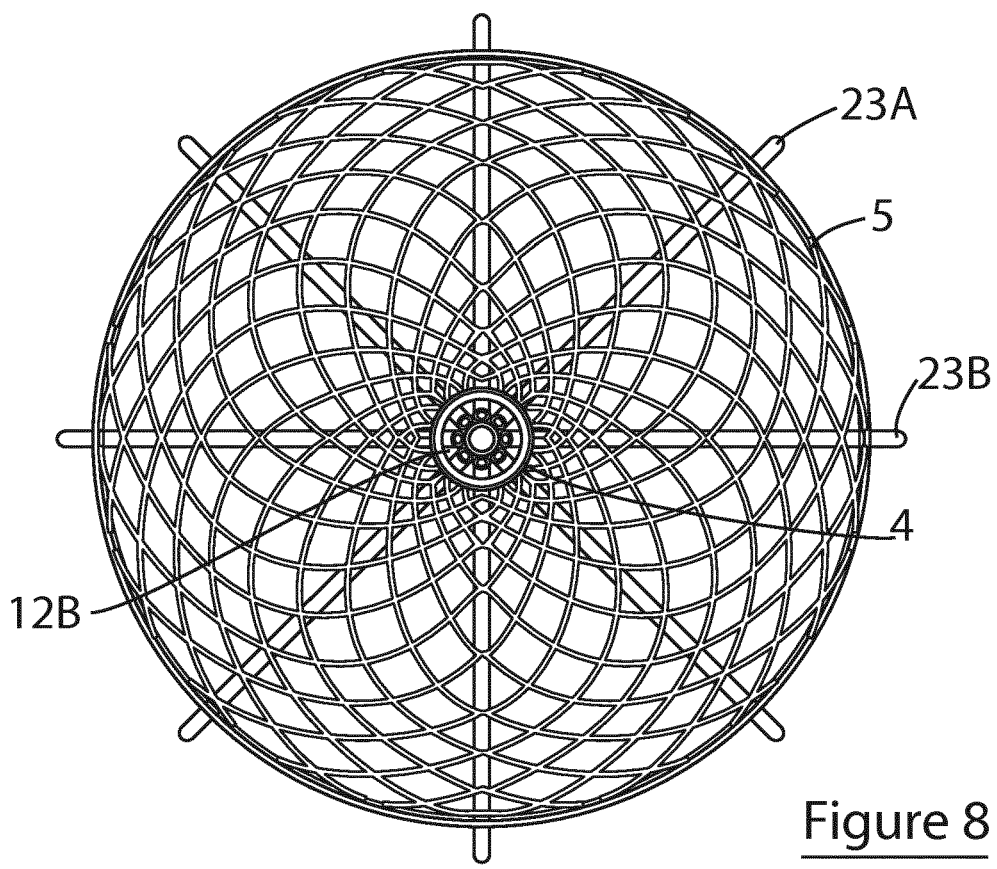

Referring to FIGS. 5 to 8, an alternative embodiment of the device of the invention is described, in which parts identified with reference to FIGS. 1 to 4 are assigned the same reference numerals. This embodiment, which is indicated generally by reference numeral 20, is substantially the same as the embodiment of FIGS. 1 to 4 except that the energy delivery element 6 is a radially expansible body 21 formed from a plurality of outwardly curved elements 23 that when deployed assume a "palm-tree" shape. The elements 23 are dimensioned to project slightly through the radially expansible element 5 when deployed, as shown in FIGS. 5 and 6. In addition, in this embodiment, the sensor is integrally formed with the energy delivery element, where some of the curved elements 23 are tissue ablation electrodes 23A and some are optical sensors 23B. Although not illustrated, the radially expansible body 21 is configured for adjustment from a contracted delivery configuration to an expanded deployed configuration shown in FIG. 5. A delivery sheath configured to cover the radially expansible body 21 and maintain it in a contracted delivery configuration during transluminal delivery is described in more detail below. The cover 13 is omitted from these illustrations to allow the proximal end of the radially expansible element 5 to be viewed.

Referring now to FIGS. 9A to 9F, the use of the device of FIG. 1 to occlude and devascularize the human LAA is described in detail, in which parts identified with reference to the embodiment of FIGS. 1 to 4 are assigned the same reference numerals. Although the use is described with reference to the embodiment of FIGS. 1 to 4, it will be appreciated that the device of FIGS. 5-8 is used in the same way.

Figure 9A:
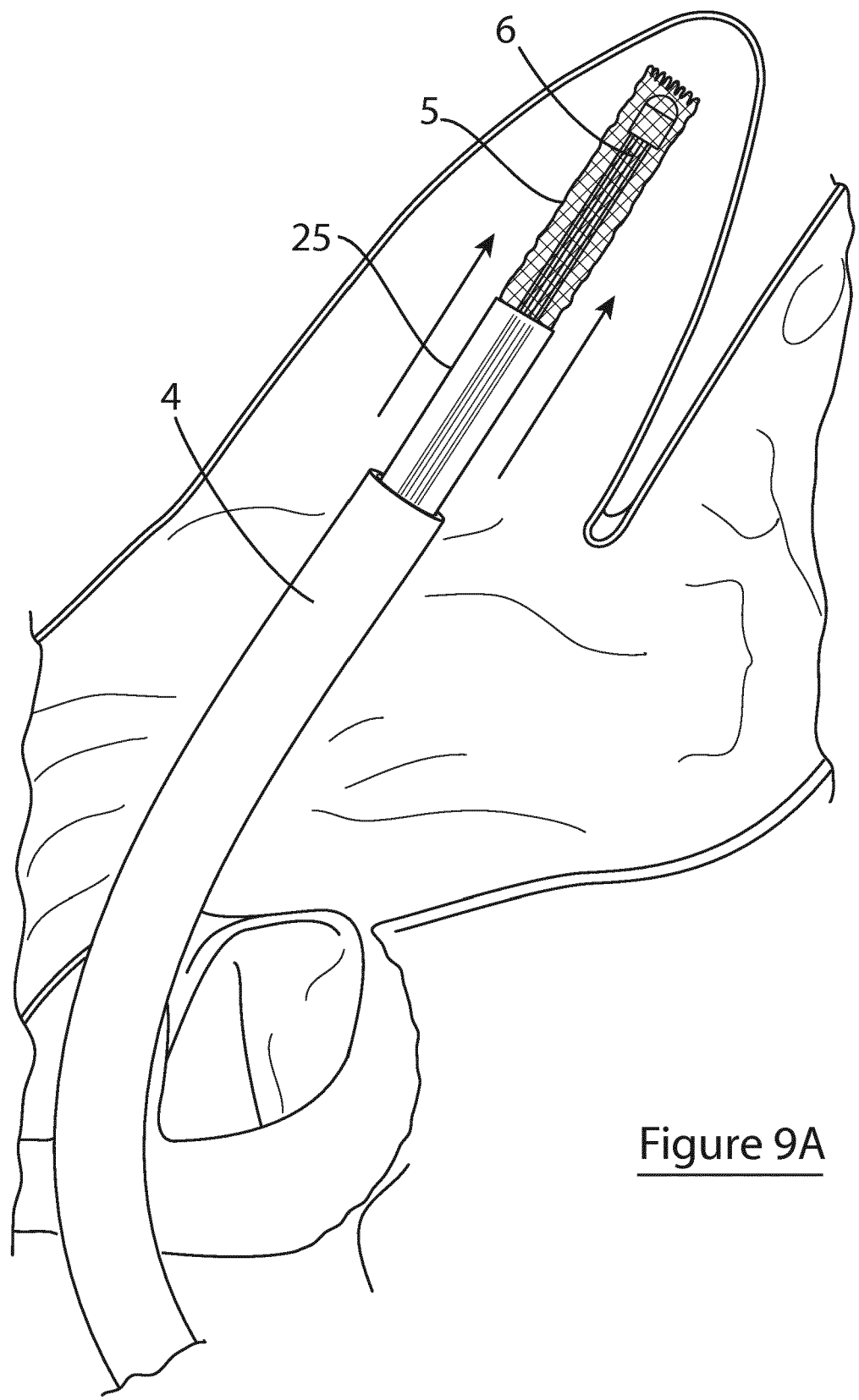
FIGS. 9A to 9F are illustrations of the use of the device of FIG. 1 in the occlusion and devascularisation of a human Left Arterial Appendage (LAA)

FIG. 9A shows the device of FIG. 1 disposed in the LAA in a partial delivery configuration, with the radially expansible element 5 and energy delivery element 6 in a contracted configuration. A delivery sheath 25, is provided within the catheter member 4 and axially adjustable from a first position (not shown) where it covers the radially expansible element 5 and energy delivery element 6 to second position shown in FIG. 9A where it has been partially axially retracted to expose the radially expansible element 5 and energy delivery element 6, allowing them to be deployed.

Figure 9B:
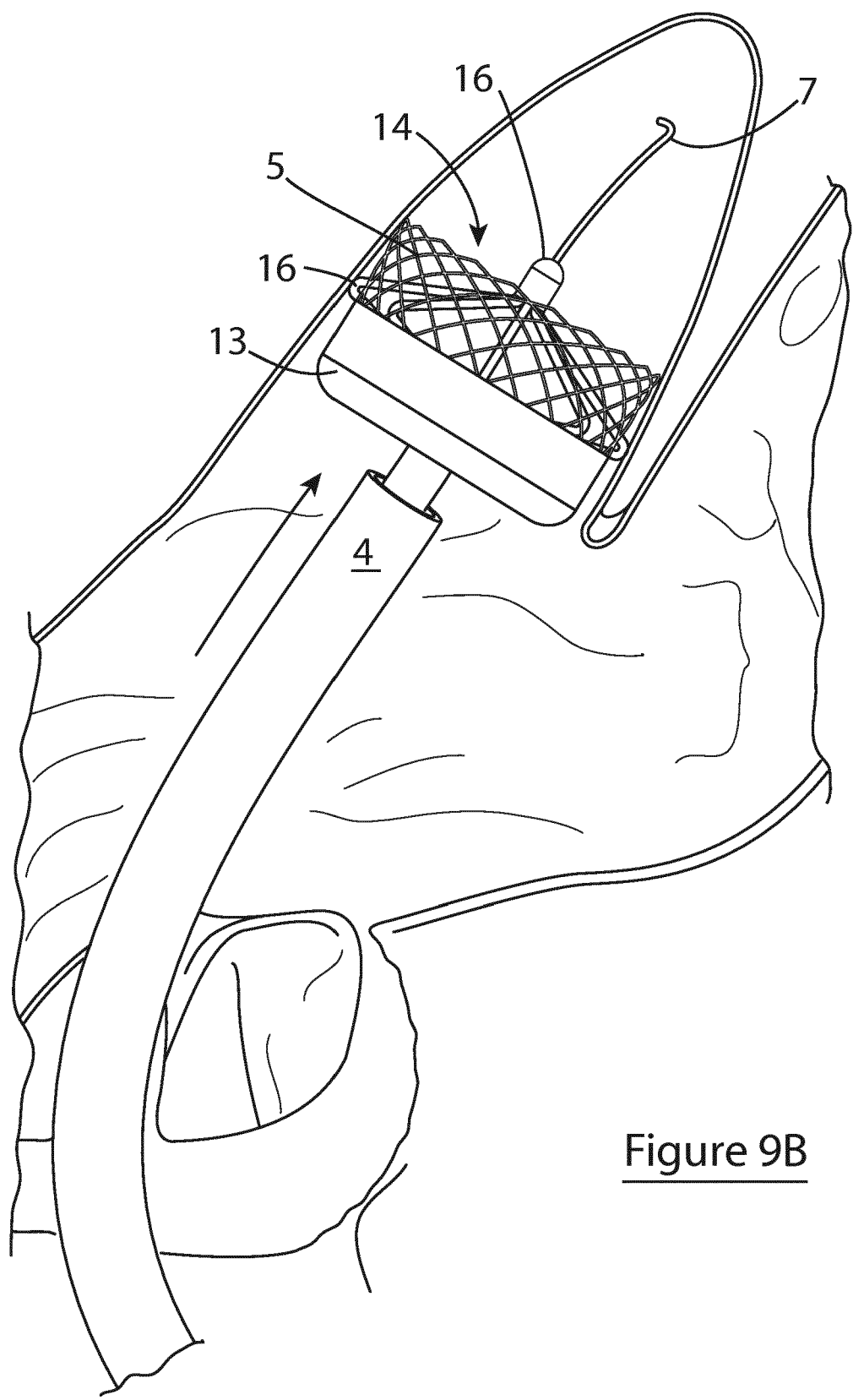
Figure 9C:
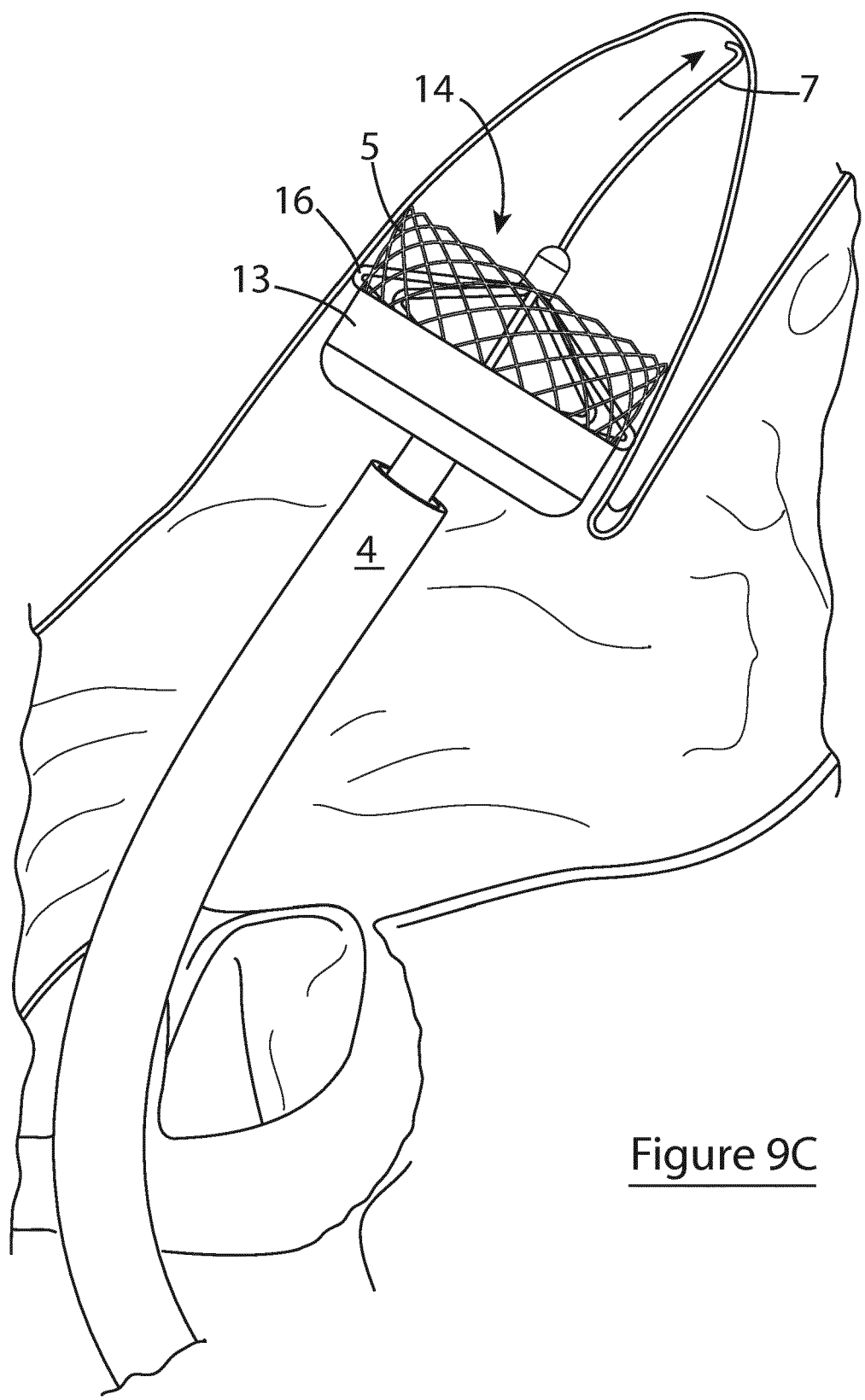
Figure 9D:
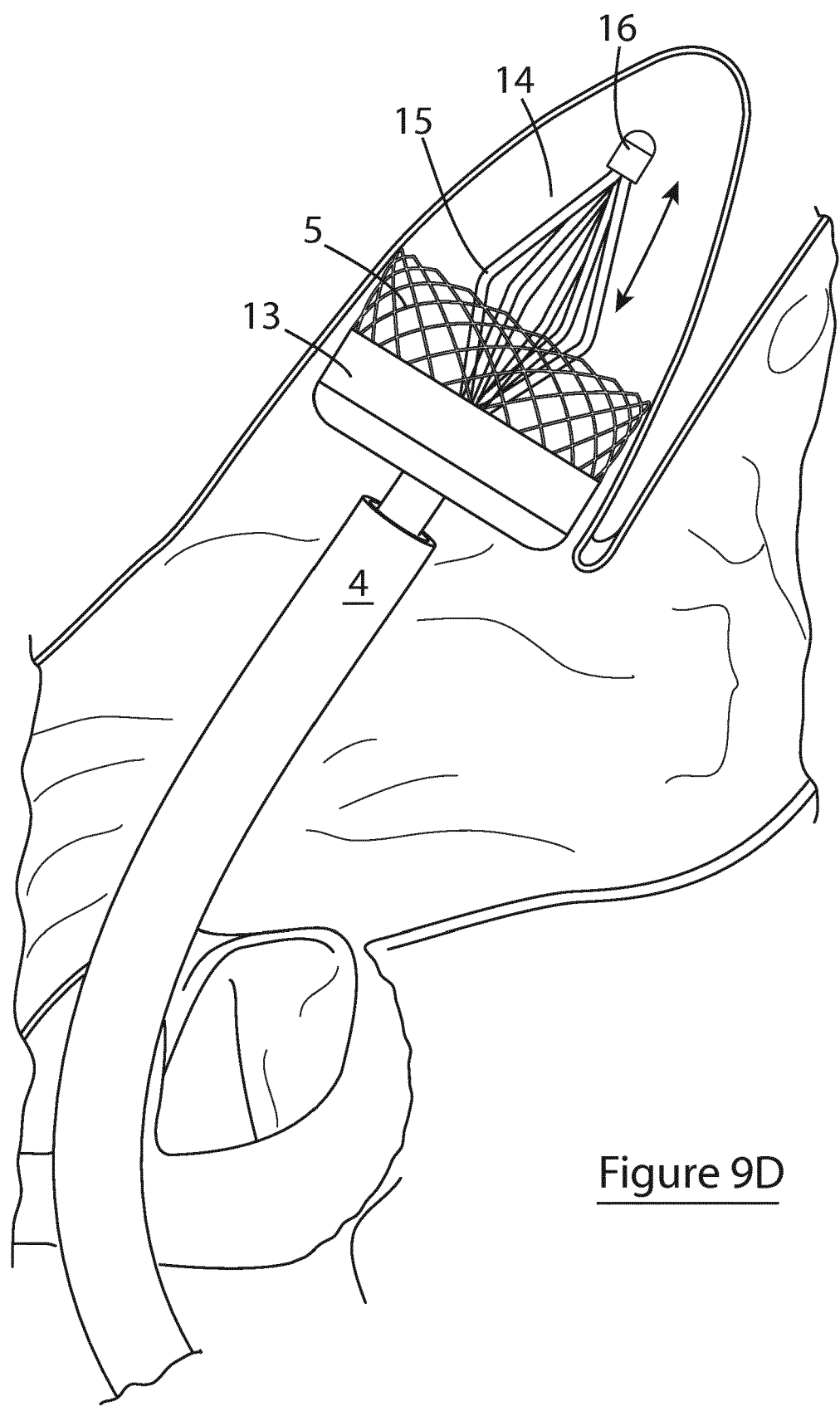
Figure 9E:
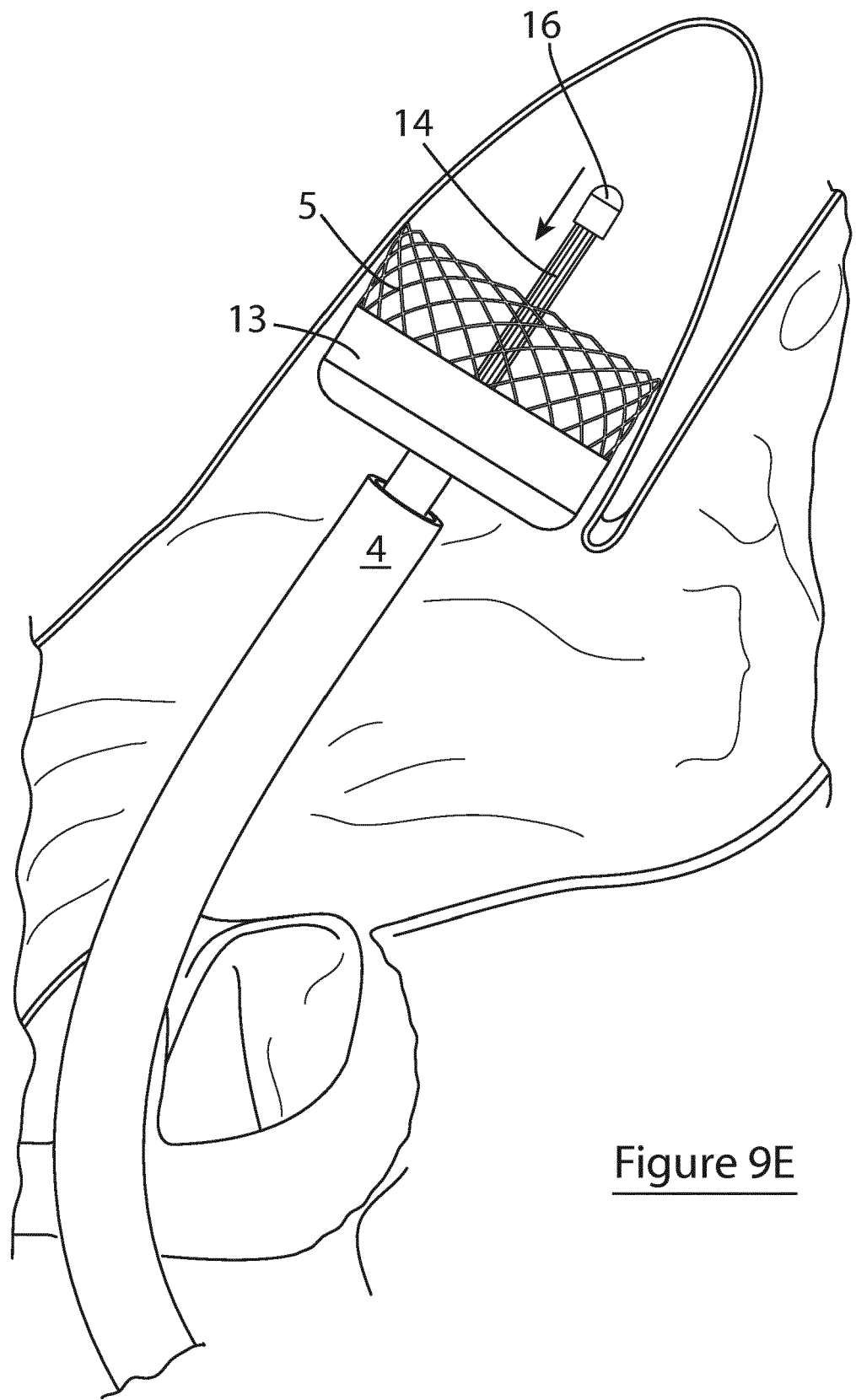
Figure 9F:
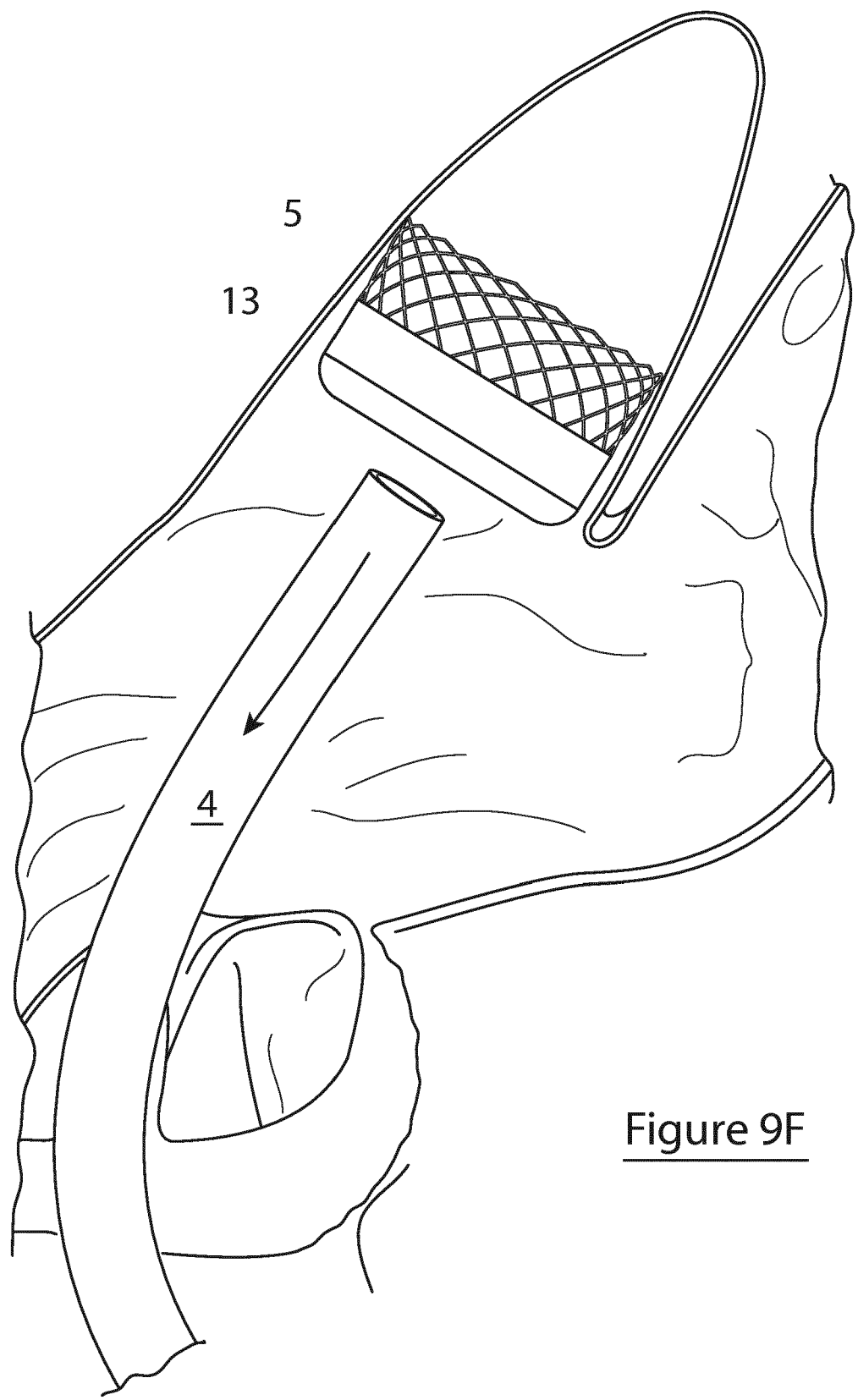

FIG. 9B shows the delivery sheath 25 fully retracted into the catheter member 4, and the radially expansible element 5 deployed to bear against the surrounding tissue of the LAA sealing the LAA distally of the radially expansible element. The optical sensor 7 has been axially extended through the radially expansible element 5 and connecting hub 16 to a position shown in FIG. 9C where the sensing end of the sensor is in contact with the distal wall of the LAA. In addition, the energy delivering radially expansible body 14 has been deployed with the elbows 16 of the V-shaped elements 15 projecting through the mesh of the radially expansible element 5 and in contact with the tissue surrounding the radially expansible element. Once the surgeon is satisfied that the device is positioned correctly and securely, and that the sensor and energy delivery elements have also been positioned correctly, the device can be actuated to deliver energy to the tissue ablation electrodes to ablate the tissue of the wall of the LAA surrounding the radially expansible element, while also sensing changes in blood flow in the wall of the LAA using the sensor 7. Once the surgeon has detected via the sensor 7 that complete devascularisation of the LAA has taken place, energy delivery to the tissue ablation electrodes can be stopped. At this point, the surgeon will know that the LAA has been devascularized, and that the therapy is complete.

Referring to FIGS. 9D to 9F, the energy delivering radially expansible body 15 and sensor 7 are then axially retracted from the therapy configuration into the delivery sheath 25 and catheter member 3. FIG. 9D shows the initial adjustment of the body 15 into a contracted configuration (FIG. 9E) and the axial retraction of the sensor 7 into the catheter member 3. The body 15 is then fully retracted into the catheter member 3, which is then remotely detached from the radially expansible element 5 (FIG. 9F) before the catheter member is transluminally withdrawn from the left atrium, leaving the radially expansible element 5 in-situ in the now devascularized LAA.

It will be appreciated that the device may include a processor and an energy controller configured to control the delivery of energy to the ablation electrodes. For example, the energy controller may be configured for electrical connection with an energy source, and configured to control the number of heating cycles, and the length of each heating cycle. The processor may be operatively connected to the sensor and energy controller and may be configured to actuate the energy controller in response to signals received from the sensor. The sensor may include a blood flow sensor, and optionally a tissue temperature sensor. Thus, if the blood flow sensor detects blood flow in the LAA, the processor may be configured to actuate the energy controller to continue the heating cycles. Likewise, if the blood flow sensor detects no blood flow in the LAA, the processor may be configured to actuate the energy controller to discontinue the heating cycles. If the temperature sensor detects that the temperature in the tissue is too high, the processor may be configured to actuate the energy controller to shorted the heating cycles, or if the temperature sensor detects that the temperature in the tissue is too low, the processor may be configured to actuate the energy controller to lengthen the heating cycles.

Figure 10A:
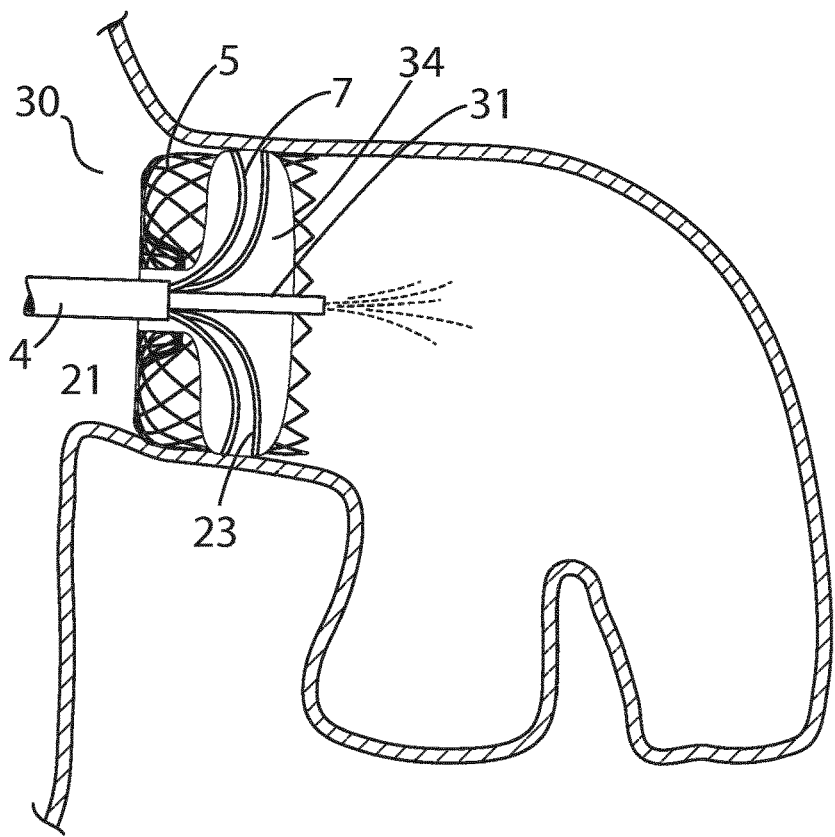
FIGS. 10A and 10B show an alternative embodiment of the device of the invention incorporating an inflatable balloon configured for inflation within the radially expansible element.
Figure 10B:
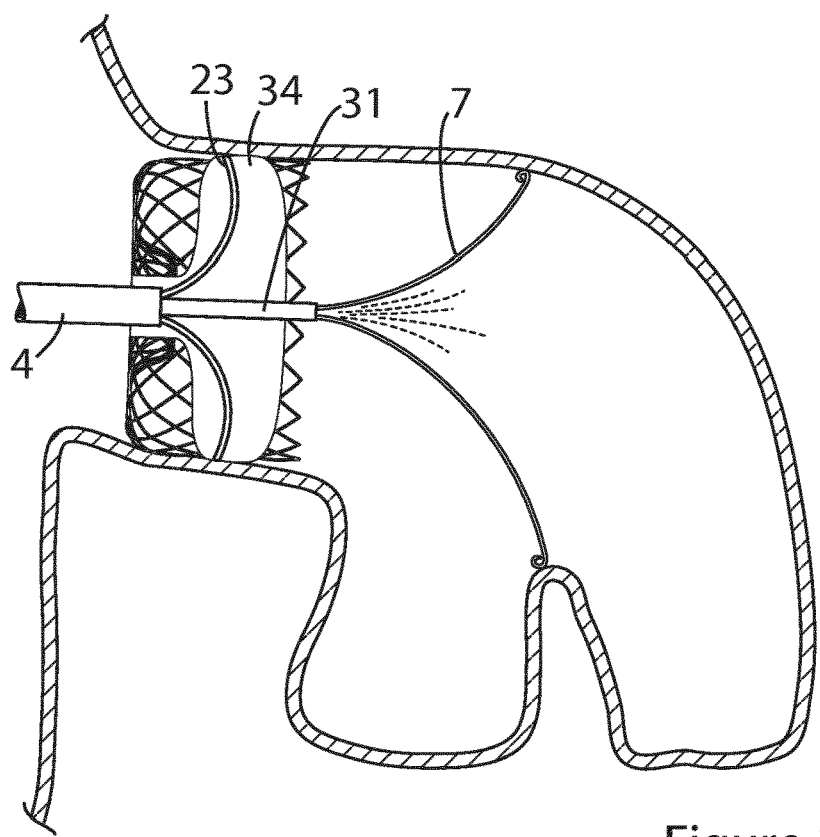

Referring to FIGS. 10A to 10B, an alternative embodiment of the device of the invention is described, in which parts described with reference to the previous embodiments are assigned the same reference numerals. In this embodiment, the device 30 is substantially the same as the device described with reference to FIG. 5, but comprises an axial conduit 31 that extends distally from the catheter member 3 through the radially expansible element 5. The conduit includes one or more flushing tubes, each having a distal outlet. The purpose of this tube or tubes is to flush saline solution into the LAA distally of the radially expansible element 5, to dilute blood in the LAA and in some cases remove the blood, or clots, from the LAA. The tube may also draw a vacuum in the LAA. This has been found to improve the accuracy of the sensor 7, especially when the sensor is an optical sensor. The device 30 also comprises an inflatable balloon 34 that is mounted on the conduit 31 within the radially expansible element 5, configured to inflate and seal the LAA to prevent flushing fluid escape in the LAA, and the energy delivering radially expansible body 21 is disposed within the balloon to prevent the flushing liquid coming into contact with the electrode elements 23. In addition, as indicated in FIG. 10B, the sensors 7 may be disposed within the balloon 34, or may extend axially from the catheter member 3 through the conduit 31.

Figure 11A:
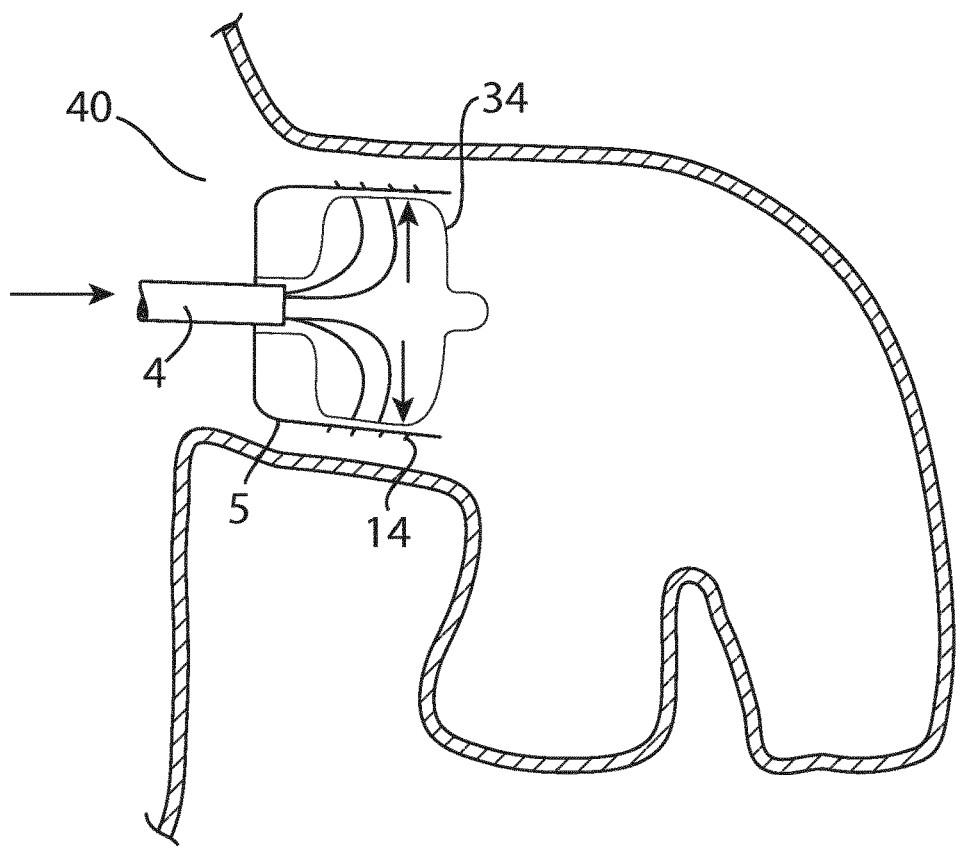
FIGS. 11A and 11B show an alternative embodiment of the device of the invention similar to the embodiment of FIG. 10 and including anchors on the radially expansible element.

Referring to FIGS. 11A, an alternative embodiment of the device of the invention is described, in which parts described with reference to the previous embodiments are assigned the same reference numerals. In this embodiment, the device 40 is substantially the same as the device described with reference to FIG. 10, except that the radially expansible element 5 includes a series of circumferentially positioned anchors 41 configured to engage the tissue when the balloon 34 expands.

Figure 11B:
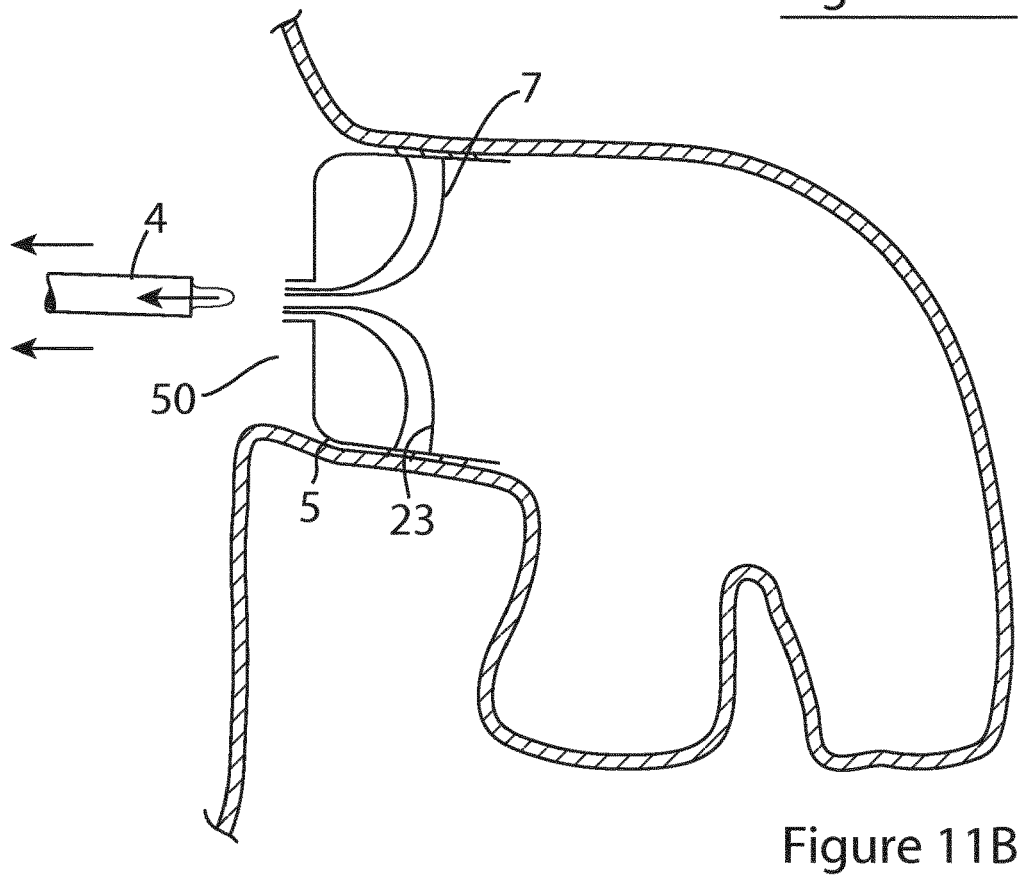

FIG. 11B illustrates an embodiment of the device of the invention indicated generally by the reference numeral 50 in which the energy delivery element 23 and sensor 7 are attached to the radially expansible element 5 and are left in-situ when the catheter member 4 is detached from the occlusion apparatus.

Figure 12A:
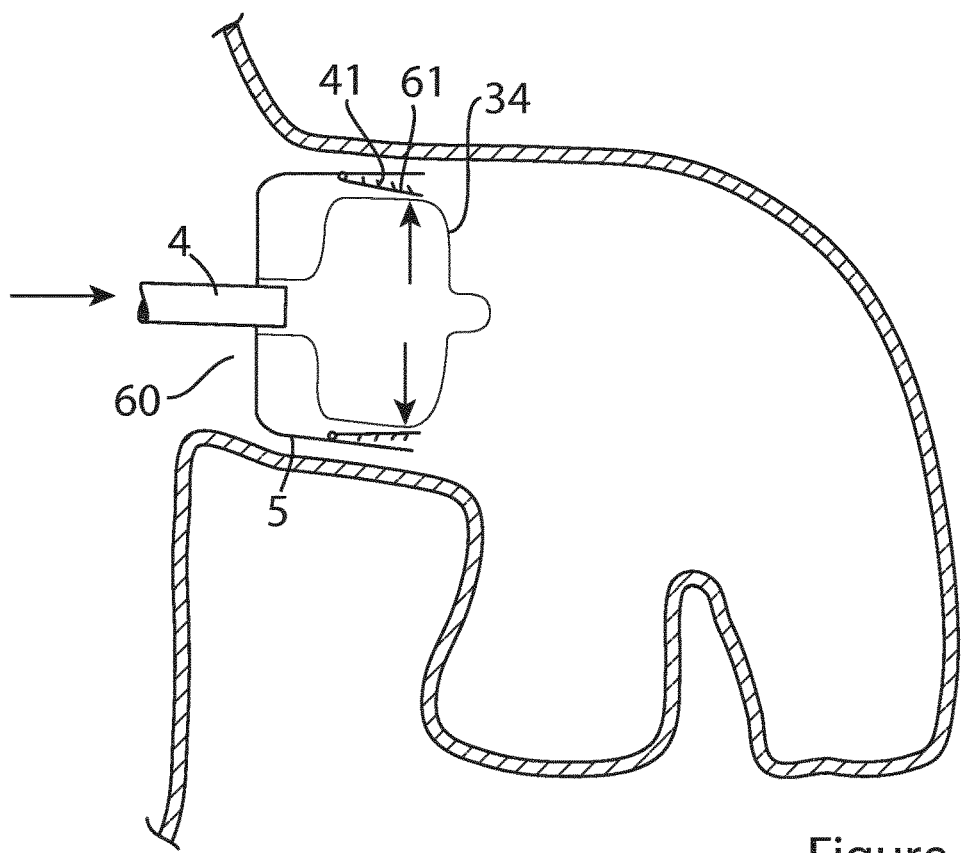
FIGS. 12A and 12B show an alternative embodiment of the device of the invention to the embodiment of FIG. 11 and including hinged side panels on the radially expansible element.
Figure 12B:
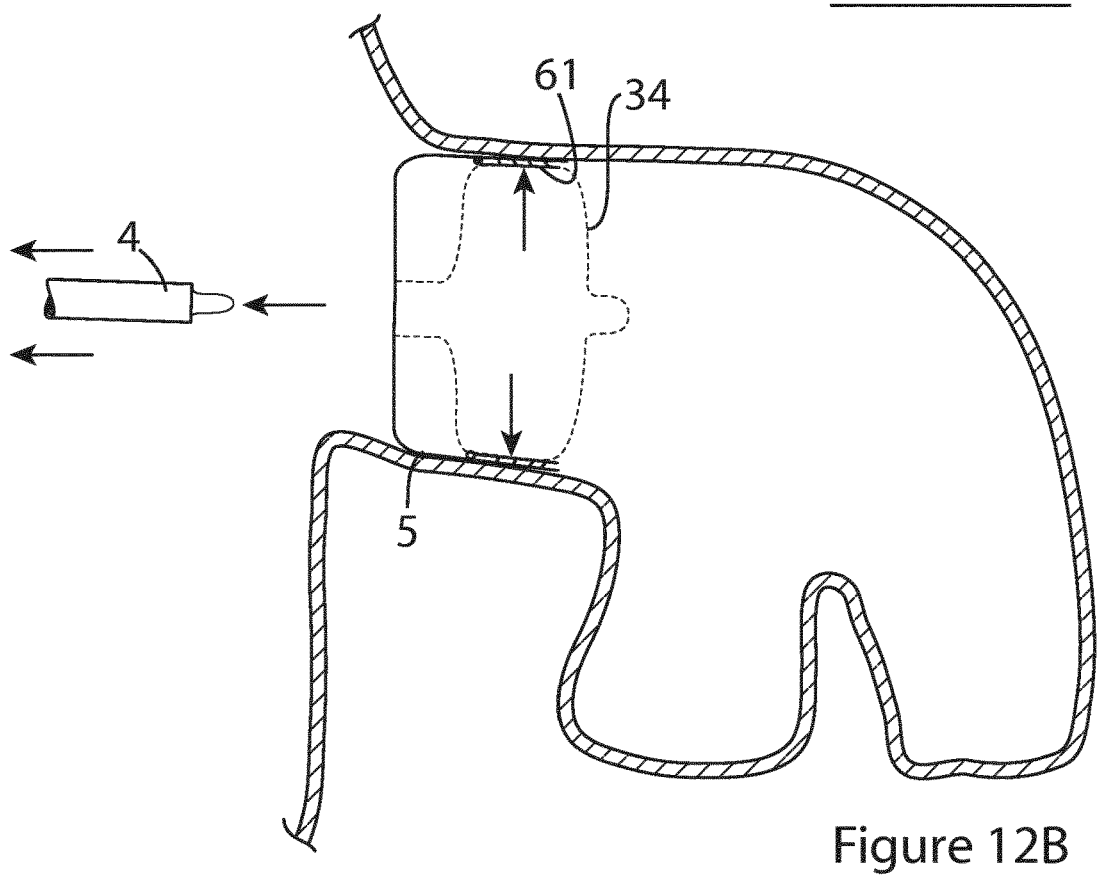

Referring to FIGS. 12A to 12B, an alternative embodiment of the device of the invention is described, in which parts described with reference to the previous embodiments are assigned the same reference numerals. In this embodiment, the device 60 is substantially the same as the device described with reference to FIG. 11, except that the radially expansible element 5 comprises two hingedly attached side panels 61 that are adjustable from an inwardly depending position shown in FIG. 12A to an outwardly depending, wall engaging, position shown in FIG. 12B, and having a plurality of anchors 41 disposed on the panels. In this embodiment, the anchors cannot engage the wall of the body lumen until the balloon is inflated which pushes the sidewall portions radially outwardly and into engagement with the tissue as shown in FIG. 12B, locking the radially expansible member in-situ in the body lumen. In this embodiment, the energy delivery element includes an electrical circuit which is completed when the sidewall portions are adjusted from the inwardly depending position to the outwardly depending, wall engaging, position.

Figure 13:
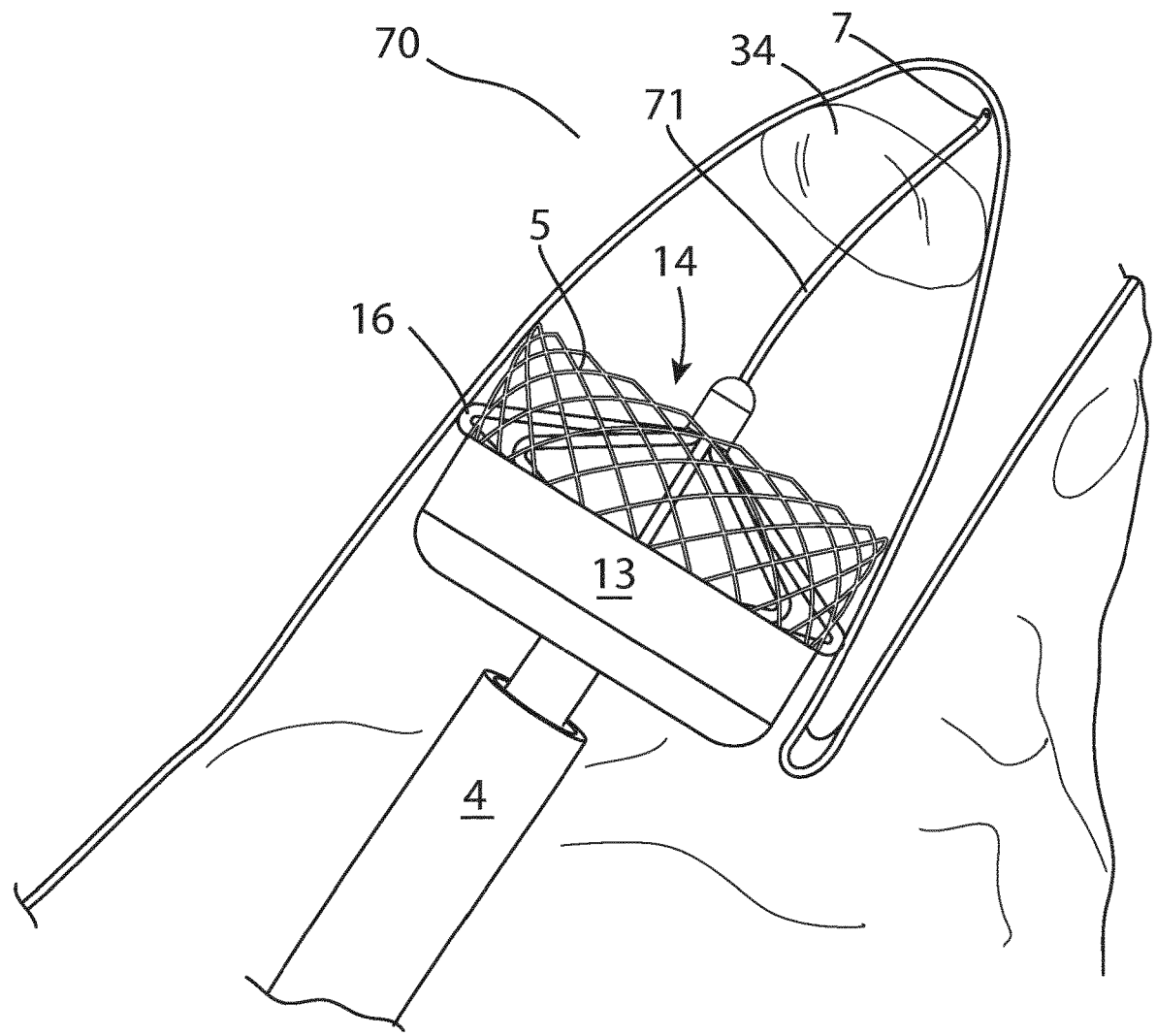
FIG. 13 shows an alternative embodiment of the device of the invention, shown in-situ in the human Left Atrial Appendage, and incorporating a balloon configured for inflation in the LAA distal of the radially expansible element.

Referring to FIG. 13, an alternative embodiment of the device of the invention is illustrated, indicated generally by the reference numeral 70, in which parts identified with reference to the previous embodiments are assigned the same reference numerals. This embodiment is substantially the same as the embodiment illustrated in FIGS. 1-4, except that the device includes a conduit 71 that extends distally of the radially expansible element 5 and comprises an inflatable balloon 34 configured for inflation distally in the LAA to occlude a distal part of the LAA. The conduit 71 also includes one or more flushing tubes (not shown) and a sensor 7 for detecting blood flow in the distal part of the LAA. In use, the device is deployed as described previously, and the sensor 7 is axially extended deep into the LAA until it comes into contact with the distal wall of the LAA. the balloon is then inflated, and the flushing tubes are employed to flush the distal part of the LAA with saline, which improves the sensors ability to detect blood flow in the tissue.

Referring to FIGS. 14A and 14B, a woven cover 13 is shown which is attached to the proximal end of the radially expansible element 5, enclosing the recess containing the connecting hub 12A. The cover 13 has an overlapping flap 81 which functions as a re-closable aperture in the cover. FIGS. 15A and 15B illustrate the engagement between the catheter member 4 and the cover 13. In use, the catheter member 4 extends through the re-closable aperture in the cover 80 and connects to connecting hub 12A, and the re-closable aperture prevents blood entering the recess and coming into contact with the coupling, and thereby preventing a major cause of Device Related Thrombus (DRT) formation. FIGS. 16A and 16B illustrate a similar cover having an alternative design of flap 81.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A device to occlude and electrically isolate a body lumen comprising an implantable occlusion apparatus (3) operably attached to an elongated catheter member (4) configured for transluminal delivery and deployment of the occlusion apparatus in the body lumen, the occlusion apparatus comprising:
   a radially self-expansible element (5) comprising a wire mesh cage detachably attached to the elongated catheter member, and adjustable between a contracted orientation suitable for transluminal delivery and a deployed orientation configured to occlude the body lumen; and
   an energy delivery element (6, 14, 21) comprising an array of electrodes configured to deliver energy to surrounding tissue to ablate the tissue,
   in which the energy delivery element is associated with the radially expansible element and configured to be left in-situ in the body lumen when the catheter member is detached from the occlusion apparatus,
in which the array of electrodes is configured to generate an electrical map or profile of an ablation zone and the surrounding tissue electrical impedance measurements to characterize the electrical properties of the tissue as a measurement and confirmation of ablation effectiveness.

2. The device according to claim 1, comprising an emission electrode and a detection electrode that are spaced apart and configured to detect electrical impedance.

3. The device according to claim 1, in which the electrodes of the array of electrodes of the energy delivery element are disposed in a spatially intermittent manner along the circumference of the wire mesh cage.

4. The device according to claim 1, in which the device comprises a processor and an energy controller configured to control the delivery of energy to the electrodes of the array of electrodes of the energy delivery element, wherein the processor is operatively connected to a sensor and the energy controller and configured to actuate the energy controller in response to signals received from the sensor.

5. The device according to claim 1, in which the wire mesh cage comprises an axial conduit that extends distally from the catheter member through the radially expansible element.

6. The device according to claim 1, in which the wire mesh cage comprises a stepped radial force stiffness profile from distal to proximal device.

7. The device according to claim 1, in which the wire mesh cage comprises a closed proximal end having a substantially toroidal shape and an open cylindrical distal end.

8. A device according to claim 1, to occlude and electrically isolate a left atrial appendage (LAA) of the heart.

9. A device to occlude and electrically isolate a body lumen comprising an implantable occlusion apparatus (3) operably attached to an elongated catheter member (4) configured for transluminal delivery and deployment of the occlusion apparatus in the body lumen, the occlusion apparatus comprising:
   a radially self-expansible element (5) detachably attached to the elongated catheter member, and adjustable between a contracted orientation suitable for transluminal delivery and a deployed orientation configured to occlude the body lumen;
   an energy delivery element (6, 14, 21) comprising an array of electrodes configured to deliver energy to surrounding tissue to ablate the tissue; and
   a sensor configured to detect a parameter of a wall of the body lumen,
   in which the energy delivery element is associated with the radially expansible element and configured to be left in-situ in the body lumen when the catheter member is detach from the occlusion apparatus,
   in which the sensor is configured for axial movement independently of the radially expansible element, and configured for axial movement distally of the radially expansible element and retraction proximally of the radially expansible element, and the sensor extends axially through a centre of the radially expansible element.

* * * * *